(12) United States Patent
Faerman et al.

(10) Patent No.: US 7,202,211 B2
(45) Date of Patent: Apr. 10, 2007

(54) METHODS OF PREVENTING OR TREATING BRAIN ISCHEMIA OR BRAIN INJURY

(75) Inventors: Alexander Faerman, Bnei Aish (IL); Sylvia G. Kachalsky, Gan Yavne (IL); Gregory Hirsch Idelson, Maale Adumim (IL)

(73) Assignees: Astellas Pharma Inc., Tokyo (JP); Quark Biotech, Inc., Cleveland, OH (US)

( * ) Notice: Subject to any disclaimer, the term of this patent is extended or adjusted under 35 U.S.C. 154(b) by 0 days.

(21) Appl. No.: 10/371,725

(22) Filed: Feb. 20, 2003

(65) Prior Publication Data

US 2003/0219430 A1    Nov. 27, 2003

Related U.S. Application Data

(60) Provisional application No. 60/359,061, filed on Feb. 21, 2002.

(51) Int. Cl.
*A61K 38/00* (2006.01)
*A61K 49/00* (2006.01)

(52) U.S. Cl. .......................... 514/12; 514/8; 530/350; 530/416; 530/417; 424/9.1; 435/226

(58) Field of Classification Search .................. 514/12, 514/8; 530/350, 416, 417; 424/9.1; 435/226
See application file for complete search history.

(56) References Cited

U.S. PATENT DOCUMENTS

| | | |
|---|---|---|
| 4,341,762 A | 7/1982 | Haast |
| 6,307,031 B1 | 10/2001 | Lipps |
| 6,316,602 B1 | 11/2001 | Lipps |

FOREIGN PATENT DOCUMENTS

| | | |
|---|---|---|
| EP | 1101820 | 5/2001 |
| WO | WO9739133 | 10/1997 |
| WO | WO0075661 | 12/2000 |
| WO | WO0163293 | 8/2001 |

OTHER PUBLICATIONS

Dodds et al., Neuronal Pentraxin Receptor, A Novel Putative Integral Membrane Pentraxin That Interacts with Neuronal Pentraxin 1 and 2 and Taipoxin-associated Calcium-building Protein 49. *J. Biol. Chem.* 272(34):21488-21494 (1997).
Fohlman et al., Taipoxin, an Extremely Potent Presynaptic Neurotixin from the Venom of the Australian Snake Taipan (*Oxyuranus s. scutellatus*). *Eur. J. Biochem.* 68:457-469 (1976).
Kirkpatrick et al., Biochemical Interactions of the Neuronal Pentraxins. *J. Biol. Chem.* 275(23):17786-17792 (2000).
Lipps, Isolation of subunits, α, β and γ of the complex taipoxin from the venom of Australian taipan snake (*Oxyuranus s. scutellatus*): characterization of β taipoxin as a potent mitogen. *Toxicon.* 38:1845-1854 (2000).
O'Brien et al., Synaptic Clustering of AMPA Receptors by the Extracellular Immediate-Early Gene Product Narp. *Neuron.* 23:309-323 (1999).
Tsui et al., Narp, a Novel Member of the Pentraxin Family, Promotes Neurite Outgrowth and Is Dynamically Regulated by Neuronal Activity. *J. Neurosci.* 16(8):2463-2478 (1996).
Alape-Giron et al., (1999), "Elapid Venom Toxins: Multiple Recruitments of Ancient Scaffolds," *Eur. J. Biochem.*, vol. 259, pp. 225-234 (Exhibit 1); and.
Tzeng et al., (Sep. 15, 1989), "Taipoxin-Binding Protein on Synaptic Membranes: Identification by Affinity Labeling," *Biochemical and Biophysical Research Communications*, vol. 165, No. 2, pp. 689-694 (Exhibit 2).

*Primary Examiner*—Chih-Min Kam
(74) *Attorney, Agent, or Firm*—John P. White; Cooper & Dunham LLP

(57) ABSTRACT

The present invention relates to use of Narp inhibitor in order to promote or enhance recovery from ischemic events, particularly focal ischemia of the central nervous system, as well as for preventing or diminishing chronic degenerative changes.

18 Claims, 9 Drawing Sheets

Figure 1A
Human Narp cDNA (SEQ ID No: 1) and corresponding polypeptide (SEQ ID No: 2)

```
   1 agcgcggtgggtgcggctgtgagacggcaggagacttctgccccgcggtgcacgcgaccc
  61 tcgagacgacagcgcggctactgccagcagcgaaggcgcctcccgcggagcgcccagacg
 121 gcgcccgctcgcccatgccgagctgagcgcggcagcggcggcgggatgctggcgctgctg
   1                                                 M  L  A  L  L
 181 gccgccagcgtggcgctcgccgtggccgctggggcccaggacagcccggcgcccggtagc
   6  A  A  S  V  A  L  A  V  A  A  G  A  Q  D  S  P  A  P  G  S
 241 cgcttcgtgtgcacggcactgcccccagaggcggtgcacgccggctgcccgctgcccgcg
  26  R  F  V  C  T  A  L  P  P  E  A  V  H  A  G  C  P  L  P  A
 301 atgcccatgcagggcggcgcgcagagtcccgaggaggagctgagggccgcggtgctgcag
  46  M  P  M  Q  G  G  A  Q  S  P  E  E  E  L  R  A  A  V  L  Q
 361 ctgcgcgagaccgtcgtgcagcagaaggagacgctgggcgcgcagcgcgaggccatccgc
  66  L  R  E  T  V  V  Q  Q  K  E  T  L  G  A  Q  R  E  A  I  R
 421 gagctcacgggcaagctagcgcgctgcgaggggctggcgggcggcaaggcgcgcggcgcg
  86  E  L  T  G  K  L  A  R  C  E  G  L  A  G  G  K  A  R  G  A
 481 ggggccacgggcaaggacactatgggcgacctgccgcgggaccccggccacgtcgtggag
 106  G  A  T  G  K  D  T  M  G  D  L  P  R  D  P  G  H  V  V  E
 541 cagctcagccgctcgctgcagaccctcaaggaccgcctggagagcctcgagcaccagctc
 126  Q  L  S  R  S  L  Q  T  L  K  D  R  L  E  S  L  E  H  Q  L
 601 agagcaaacgtgtccaatgctgggctgcccggcgacttccgcgaggtgctccagcagcgg
 146  R  A  N  V  S  N  A  G  L  P  G  D  F  R  E  V  L  Q  Q  R
 661 ctgggggagctggagaggcagcttctgcgcaaggtggcagagctggaggacgagaagtcc
 166  L  G  E  L  E  R  Q  L  L  R  K  V  A  E  L  E  D  E  K  S
 721 ctgctgcacaatgagacctcggctcaccggcagaagaccgagagcaccctgaacgcgctg
 186  L  L  H  N  E  T  S  A  H  R  Q  K  T  E  S  T  L  N  A  L
 781 ctgcagagggtcaccgagctggagcgaggcaatagcgcctttaagtcaccagatgcgttc
 206  L  Q  R  V  T  E  L  E  R  G  N  S  A  F  K  S  P  D  A  F
 841 aaggtgtccctcccactccgcacaaactacctatacggcaagatcaagaagacgctgcct
 226  K  V  S  L  P  L  R  T  N  Y  L  Y  G  K  I  K  K  T  L  P
 901 gagctgtacgccttcaccatctgcctgtggctgcggtccagcgcctcaccaggcattggc
 246  E  L  Y  A  F  T  I  C  L  W  L  R  S  S  A  S  P  G  I  G
 961 accccttctcctatgcggtgccagggcaggccaacgagatcgtgctgatcgagtggggc
 266  T  P  F  S  Y  A  V  P  G  Q  A  N  E  I  V  L  I  E  W  G
1021 aacaaccccatcgagctgctcatcaacgacaaggttgcgcagctgccccctgtttgtcagt
 286  N  N  P  I  E  L  L  I  N  D  K  V  A  Q  L  P  L  F  V  S
1081 gacggcaagtggcaccacatctgtgtcacctggacgacacgggatggcatgtgggaggca
 306  D  G  K  W  H  H  I  C  V  T  W  T  T  R  D  G  M  W  E  A
1141 ttccaggacggagagaagctgggcactggggagaacctggcccctggcacccatcaag
 326  F  Q  D  G  E  K  L  G  T  G  E  N  L  A  P  W  H  P  I  K
1201 cccggggcgtgctgatccttggacaagagcaggacaccgtggggggtaggtttgatgcc
 346  P  G  V  L  I  L  G  Q  E  D  T  V  G  G  R  F  D  A
1261 actcaggcatttgtcggggagctcagccagttcaacatatgggaccgcgtccttcgcgca
 366  T  Q  A  F  V  G  E  L  S  Q  F  N  I  W  D  R  V  L  R  A
1321 caagaaattgtcaacatcgccaactgctccacaaacatgccgggcaacatcatcccgtgg
 386  Q  E  I  V  N  I  A  N  C  S  T  N  M  P  G  N  I  I  P  W
1381 gtggacaataacgtcgatgtgttcggaggggcctccaagtggcccgtggagacgtgtgag
 406  V  D  N  N  V  D  V  F  G  G  A  S  K  W  P  V  E  T  C  E
1441 gagcgtctccttgacttgtagccgcctttctcctctgtccaggaggccgggatcaggctgt
 426  E  R  L  L  D  L  *
1501 tgccatggaagttcagggccatagactgccccacttaaactcttgtcagtctgggctcag
1561 ggttcccagagctcattcccaggaatctctaagaccagggctggggcagtgtctgtcac
1621 tggcttgtttgttccctaccaatattctgttgctgtttgaagtagtgccagggtcccctg
1681 ggaagatgccccaagacacctgcccaagtgggtggatatctgccttcctgctgcaagt
1741 ggaggcaggtccagcagcccctcttcagagccctgtaaatgctatcgcagcctgagtcc
```

Figure 1B

```
1801 tgccgccttccagttccttggtgtcccgtgcaccccttctgtctgtcccctttcatggct
1861 gtgcagccgtcccgctggagtggccatgtcccttgtgcattgagtgcatccccgctggtg
1921 actaagctcgcagcaagcggctaccccccgatctgcaaaagggcctctccctttgtgttc
1981 tatacattgtgaatcttcccgtctgaagaacgcccagcctgcccagacaaagccccgcct
2041 tccccaaagcagaggggctgtctgtgtctccagaaagggggacatcggggggggaggggggc
2101 tcagaaaggagaagggctgtgatctccggtcccttcccccatcatccttccttagactga
2161 tgctttgactgaatcatcactagctatggcattaaaaggcctctcttctcatctggtgcc
2221 aaaggttccgttgcagcttttacaaccatccggtgtggtttggaggttttgttttttt
2281 ttttcccaacagaaaagaacagccattagaagaaggctcccattttctgatgttccgccc
2341 cactgtgaagagtgtgctcgttttaaattcatgttgattcttgtaagcactggactgtct
2401 tcatcaagtatttccctacagaactcctcaagaaaacagagatcatttggctagagattg
2461 tctgagtgactccaagctactcactgtattggacgggagtagtaatttattttaaagata
2521 aagtgactaagtggggaaatttataaagctaaatattatatattttatttttcatacatg
2581 tttgaagtgcaaatctgtggatattccatttgtaggaccaagtcgacatgcccatcctga
2641 cattgtatgctacgagaactcttctgatgatggaatttcgattaaagtgcactgaaagat
2701 aaaaaaaaaaaaaaaaaaaaaaaaaaaaaaaaaaaaaaaaa
```

Figure 2A
Rat Narp cDNA (SEQ ID No.: 3) and corresponding polypeptide (SEQ ID No.: 4)

```
   1 tggtgctggcgtttccctgcttgcacgcggttccctcgagcgccgctccgaccgacgtag
  61 ccggccgcgaaggcgcccagacggcaagccagcgacccatgctgaagtgagcgcccaggt
 121 cagcgagatgctggcgctgctgaccgccggcgtggcgctcgccgtggccgcgggacaagc
   1             M   L   A   L   L   T   A   G   V   A   L   A   V   A   A   G   Q   A
 181 ccaggataacccgatacctggcagtcgcttcgtgtgcaccgcgctgccccccgaagcggc
  19     Q   D   N   P   I   P   G   S   R   F   V   C   T   A   L   P   P   E   A   A
 241 gcgcgccggctgcccgctgcccgcgatgcccatgcagggaggcgcgctgagccctgagga
  39     R   A   G   C   P   L   P   A   M   P   M   Q   G   G   A   L   S   P   E   E
 301 ggagctgcgagccgctgtgctgcactggcgcgagaccgtcgtgcagcagaaggagacgct
  59     E   L   R   A   A   V   L   H   W   R   E   T   V   V   Q   Q   K   E   T   L
 361 gggcgctcagcgagaagccatcgagaactcaccagcaagctggcccgctgtgagggact
  79     G   A   Q   R   E   A   I   R   E   L   T   S   K   L   A   R   C   E   G   L
 421 agccggcggtaaggcgcgcggcacgggggccacgggcaaggacaccatgggcgacctgcc
  99     A   G   G   K   A   R   G   T   G   A   T   G   K   D   T   M   G   D   L   P
 481 gcgggacccgggccacgtcgtggagcagcttagccgctcgctgcagaccctcaaggaccg
 119     R   D   P   G   H   V   V   E   Q   L   S   R   S   L   Q   T   L   K   D   R
 541 cttggagagcctcgagctccaactccacaccaacgcgtctaatgccgggctgccgagcga
 139     L   E   S   L   E   L   Q   L   H   T   N   A   S   N   A   G   L   P   S   D
 601 cttccgagaggtgctccagcggaggctgggggagctggagaggcagttgctacgcaaggt
 159     F   R   E   V   L   Q   R   R   L   G   E   L   E   R   Q   L   L   R   K   V
 661 ggccgagctggaagacgagaagtccctgctccacaatgagacctcggctgcaccggcagaa
 179     A   E   L   E   D   E   K   S   L   L   H   N   E   T   S   A   H   R   Q   K
 721 gacagagaacacactgaatgcactgctgcagagggtgactgagctggagagaggcaacag
 199     T   E   N   T   L   N   A   L   L   Q   R   V   T   E   L   E   R   G   N   S
 781 tgcattcaagtcaccagatgcattcaaagtgtccctccctctccgtacaaactacctata
 219     A   F   K   S   P   D   A   F   K   V   S   L   P   L   R   T   N   Y   L   Y
 841 cggcaagatcaagaagacgttgcccgagctgtatgccttcaccatctgcctgtggctgcg
 239     G   K   I   K   K   T   L   P   E   L   Y   A   F   T   I   C   L   W   L   R
 901 gtccagcgcctcgccaggcatcggcacgccattctcctacgctgtgcctgggcaagccaa
 259     S   S   A   S   P   G   I   G   T   P   F   S   Y   A   V   P   G   Q   A   N
 961 tgagattgtgctgatagagtggggtaacaatcccatagagctgcttatcaacgacaaggt
 279     E   I   V   L   I   E   W   G   N   N   P   I   E   L   L   I   N   D   K   V
1021 cgcacagctgcccctgtttgtcagcgatggcaagtggcaccatatctgcatcacctggac
 299     A   Q   L   P   L   F   V   S   D   G   K   W   H   H   I   C   I   T   W   T
1081 cactcgagacggcatgtgggaagcattccaggacggggagaagctgggcaccggggagaa
 319     T   R   D   G   M   W   E   A   F   Q   D   G   E   K   L   G   T   G   E   N
1141 cctggcaccctggcatcccatcaagccagggggtgtgctcatcctggggcaggagcagga
 339     L   A   P   W   H   P   I   K   P   G   G   V   L   I   L   G   Q   E   Q   D
1201 cactgtgggaggcagatttgatgccacacaggccttcgttggagagcttagccagttcaa
 359     T   V   G   G   R   F   D   A   T   Q   A   F   V   G   E   L   S   Q   F   N
1261 catatgggaccgtgtcctccgggcacaagagatcatcaacatcgccaactgctccacgaa
 379     I   W   D   R   V   L   R   A   Q   E   I   I   N   I   A   N   C   S   T   N
1321 catgcctggaaacatcatcccatgggtggacaacaatgtcgatgtgtttggagggcttc
 399     M   P   G   N   I   I   P   W   V   D   N   N   V   D   V   F   G   G   A   S
1381 caagtggcctgtggagacgtgcgaagagcgtctcctggacttgtagctaccttctccctg
 419     K   W   P   V   E   T   C   E   E   R   L   L   D   L   *
1441 tcccagaggccaagagcgggctgttctggggagttcaaggcatctattcccgagttcaac
1501 taaaatctctggcctgagtaggaaagaaccagagcccctaaggcaggctgtgtggcctcc
1561 tttgtcttaggctcctatgttcttactgctttgttctttggtgggaagtgaccgaagccc
1621 tgggaagagtcctgagccacttcctgctggggtttctagtaaagtctgtgagcctctcca
1681 cccctcctgtaaatgctagtgcaacccagccctgcctgtcatttggatccttagtgtct
1741 cgtgtgtgcttcccgtctgtccccttttgatggctgtgtggtcatcctaccggggtggcct
1801 gggtcccttgtgtgtgtagcacatccctgcttttgactgaacacagtgcacagaagctac
```

Figure 2B
1861 ccgcccctgaaacagggtctctccctcagtgtcatgtgcactctggtctctccctctgag
1921 gggactgcagctgctggagggccacgtgcccagacagtccccagcatccccaaagcagac
1981 cctccgccatggagaaagtcccccacagcttccccaccctctgtccacctctcagacccc
2041 acgcttctaaggaccattgctgggttggctttcaaaagctgctgctctcatctggtgcca
2101 aaagttcatttgcagcttctacaccgttctgtgtggtttggggattgactttattccccc
2161 acaaaagaggaacagccattagaagccagcctcccctccttttgatgctcagcccactgt
2221 gaagagtgagcttgcttgtaagccacattggtttctgtgagcatctgactctcccccgtc
2281 cagtatttccccggaactggagattcgagtgccattcggctgctacctgcttagtgact
2341 ccaggctgcatcatgtatcataatttatttaaagacaaagtgattcagtggggaaattt
2401 ataaagctataaatattatatatttattttcatacatgtttaaagtgcggatccatgg
2461 atgttccatttgtaggaccagcttgacgtgcccatcctgacattgtatgccacaagagct
2521 cttgtgatgatggaattttgattaaagtgcactggaagatga Figure 3A
Homology comparison of cDNA nucleotide sequences of Rat (SEQ ID No.: 3), Mouse (SEQ ID No.: 5) and Human (SEQ ID No.: 1) Narps

```
5    CLUSTAL W (1.7) multiple sequence alignmentx

NARP rat sequ           TGGTGCTGGCGTTTCCCTGCTTGCACGCGGTTCCCTCGAGCGCCGCTCCGACCGACGTAG
     mouse narp nptx2seq     ------------------------------------------------------------G
10                                                                                      *

NARP rat sequ           CCGGCCGCGAAGGCGCCCAGACGGCAAGCCAGCGACCCATGCTGAAGTGAGCGCCCAGGT
     mouse narp nptx2seq     CCGGCCGCGAAG-CGCCCAGACGGCAAACCAGCGACCCATGCTGAAGTGAGCACACAGGT
                             ************ *************** *************************  * *****
15
     NARP rat sequ           CAGCGAGATGCTGGCGCTGCTGACCGCCGGCGTGGCGCTCGCCGTGGCCGCGGGACAAGC
     mouse narp nptx2seq     CAGCGAGATGCTGGCGCTGCTGACCGTCGGCGTGGCGCTCGCCGTGGCCGCCGGACGAGC
                             ************************** ************************ ****  ***

20   NARP rat sequ           CCAGGATAACCCGATACCTGGCAGTCGCTTCGTGTGCACCGCGCTGCCCCCCGAAGCGGC
     mouse narp nptx2seq     CCAGGACAGCCCGATACCTGGCAGCCGCTTCGTGTGCACCGCGCTTGCCCCCCGAAGCGGC
                             ****** * ***************** *************** ******************

NARP rat sequ           GCGCGCCGGCTGCCCGCTGCCCGCGATGCCCATGCAGGGAGGCGCGCTGAGCCCTGAGGA
25   mouse narp nptx2seq     GCGCGCCGGTTGCCCGCTGCCCGCGATGCCCATGCAGGGAGGCGCTCTGAGCCCCGAGGA
                             ********* ************************************** *********** ** ****

NARP rat sequ           GGAGCTGCGAGCCGCTGTGCTGCACTGGCGCGAGACCGTCGTGCAGCAGAAGGAGACGCT
     mouse narp nptx2seq     GGAGCTGCGAGCCGCTGTGCTGCAGCTGCGCGAGACCGTCGTGCAGCAGAAGGAGACGCT
30                           ************************ * *********************************

NARP rat sequ           GGGCGCTCAGCGAGAAGCCATCCGAGAACTCACCAGCAAGCTGGCCCGCTGTGAGGGACT
     mouse narp nptx2seq     GGGCGCCCAGCGAGAAGCCATCCGAGAGCTCACCGGCAAGCTGGCCCGCTGCGAGGGGCT
35                           ****** ******************* ****** **************** ******* **

NARP rat sequ           AGCCGGCGGTAAGGCGCGCGGCACGGGGGCCACGGGCAAGGACACCATGGGCGACCTGCC
     mouse narp nptx2seq     GGCGGGGGGCAAGGCGCGCGGCACAGG---------CAAGGACACCATGGGCGACCTGCC
                             ** ** ** *************** **         *************************

40   NARP rat sequ           GCGGGACCCGGGCCACGTCGTGGAGCAGCTTAGCCGCTCGCTGCAGACCCTCAAGGACCG
     mouse narp nptx2seq     GCGGGACCCGGGCCACGTCGTGGAGCAGCTTAGCCGCTCCTTGCAAACCCTCAAGGACCG
                             *************************************** **** **************

NARP rat sequ           CTTGGAGAGCCTCGAGCTCCAACTCCACACCAACGCGTCTAATGCCGGGCTGCCGAGCGA
45   mouse narp nptx2seq     CTTGGAGAGCCTCGAGCTCCAGCTCCGCACAAATGTGTCTAACGCTGGGCTGCCGAGCGA
                             ********************* **** *** ** * ****** ** *************

NARP rat sequ           CTTCCGAGAGGTGCTCCAGCGGAGGCTGGGGGAGCTGGAGAGGCAGTTGCTACGCAAGGT
     mouse narp nptx2seq     CTTCCGAGAGGTGCTCCAGCGGAGGCTCGGGGAGCTGGAGAGGCAGTTGCTACGCAAGGT
50                           *************************** ********************************

NARP rat sequ           GGCCGAGCTGGAAGACGAGAAGTCCCTGCTCCACAATGAGACCTCGGCTCACCGGCAGAA
     mouse narp nptx2seq     GGCGGAGCTGGAAGATGAGAAGTCCCTGCTTCATAATGAGACCTCGGCTCACCGGCAGAA
                             *** ************ ************ ** **************************

55   NARP rat sequ           GACAGAGAACACACTGAATGCACTGCTGCAGAGGGTGACTGAGCTGGAGAGAGGCAACAG
     mouse narp nptx2seq     GACAGAGAGCACGCTGAACGCCCTGCTGCAGAGGGTGACTGAGCTGGAGCGAGGCAACAG
                             ******** *** ***** ** *************************** **********

60   NARP rat sequ           TGCATTCAAGTCACCAGATGCATTCAAAGTGTCCCTCCCTCTCCGTACAAACTACCTATA
     mouse narp nptx2seq     TGCATTCAAGTCACCAGATGCATTCAAAGTGTCCCTTCCTCTCCGTACAAACTACCTGTA
```

Figure 3B

```
                                    ******************************** ****************** **
NARP rat sequ        CGGCAAGATCAAGAAGACGTTGCCCGAGCTGTATGCCTTCACCATCTGCCTGTGGCTGCG
mouse narp nptx2seq  TGGCAAGATCAAGAAGACATTGCCTGAGCTGTACGCCTTTACCATCTGCCTGTGGCTGCG
                     ***************** ***** ******* ***** *************.********

NARP rat sequ        GTCCAGCGCCTCGCCAGGCATCGGCACGCCATTCTCCTACGCTGTGCCTGGGCAAGCCAA
mouse narp nptx2seq  GTCCAGTGCCTCGCCAGGCATCGGTACGCCATTCTCCTACGCTGTGCCCGGGCAAGCCAA
                     ****** ***************** *********************** **********

NARP rat sequ        TGAGATTGTGCTGATAGAGTGGGGTAACAATCCCATAGAGCTGCTTATCAACGACAAGGT
mouse narp nptx2seq  CGAGATTGTGCTGATAGAGTGGGGCAATAACCCCATTGAGCTGCTCATCAACGACAAGGT
                      *********************** ** ** ***** ******* **************

NARP rat sequ        CGCACAGCTGCCCCTGTTTGTCAGCGATGGCAAGTGGCACCATATCTGCATCACCTGGAC
mouse narp nptx2seq  CGCACAGCTGCCGCTGTTTGTCAGTGATGGCAAGTGGCACCACATCTGCATCACCTGGAC
                     ************ *********** ***************** ****************

NARP rat sequ        CACTCGAGACGGCATGTGGGAAGCATTCCAGGACGGGGAGAAGCTGGGCACCGGGGAGAA
mouse narp nptx2seq  CACTCGAGACGGCATGTGGGAAGCGTTCCAGGATGGGGAGAAGCTGGGCACTGGGGAAAA
                     ************************ ******** **************** ***** **

NARP rat sequ        CCTGGCACCCTGGCATCCCATCAAGCCAGGGGGTGTGCTCATCCTGGGGCAGGAGCAGGA
mouse narp nptx2seq  CCTGGCACCCTGGCACCCCATTAAGCCAGGGGGCGTGCTCATCCTGGGGCAGGAGCAGGA
                     *************** ***** *********** **************************

NARP rat sequ        CACTGTGGGAGGCAGATTTGATGCCACACAGGCCTTCGTTGGAGAGCTTAGCCAGTTCAA
mouse narp nptx2seq  CACGGTGGGAGGCAGATTTGATGCCACGCAGGCCTTTGTTGGAGAGCTCAGCCAGTTCAA
                     *** *********************** ******** *********** **********

NARP rat sequ        CATATGGGACCGTGTCCTCCGGGCACAAGAGATCATCAACATCGCCAACTGCTCCACGAA
mouse narp nptx2seq  CATATGGGACCGCGTCCTCCGGGCGCAGGAGATCATCAACATCGCCAACTGCTCCACGAA
                     ************ *********** ** *******************************

NARP rat sequ        CATGCCTGGAAACATCATCCCATGGGTGGACAACAATGTCGATGTGTTTGGAGGGGCTTC
mouse narp nptx2seq  CATGCCCGGCAACATCATCCCGTGGGTGGACAACAATGTCGATGTGTTCGGCGGGGCTTC
                     ****** ** *********** ************************** ** *******

NARP rat sequ        CAAGTGGCCTGTGGAGACGTGCGAAGAGCGTCTCCTGGACTTGTAGCTACCTTCTCCCTG
mouse narp nptx2seq  CAAGTGGCCTGTGGAGACCTGTGAAGAGCGGCTCCTGGACTTGTAGCTGCCCTCTCC--G
                     ****************** ** ******** ***************** ** *****  *

NARP rat sequ        TCCCAGAGGCCAAGAGC----GGGCTGTTCTGGGGAGTTCAAGGCATCTATTCCCGAGTT
mouse narp nptx2seq  TCCCAGAGGCCACGATCCATCGGGCTGTTCTGAGGACTTCAAGGCATCTCTTCCCCA-TT
                     ************ ** *    *********** *** ************ *****  **

NARP rat sequ        CAACTAAAATCTCTGGCCTGAGTAGGAAAGAACCAGAGCCCCTAAGGCAGGCTGTGTGGC
mouse narp nptx2seq  CACCTAAAACCTCTGGCCTGAACAGAAAAGAGCCGGAGCTC-TAATGCAGGCTGTGTGGC
                     ** ****** ***********  ** ***** ** *****  *** **************

NARP rat sequ        CTCCTTTGTCTTAGGCTCCTATGTTC-TTACTGCTTTGT------TCTTTGGTGGGAAGT
mouse narp nptx2seq  CGCCCTTGTCTTAGGCTCATTTGTTCCTTACCATTTTGTCGAGGTTTTTTGGGGGGTAGT
                     * ** ************* * ***** ****  ** ***       ***** *** ***

NARP rat sequ        GACCGAAGCCCTGGGAAGAGTCCTGAGCCACTTCCTGCTGGGGTTTCTAGTAAAGTCTGT
mouse narp nptx2seq  GACAGAATCCCTGG-AAGAGTCTTGAGCCACTTCCTGCTGGGGTTTCT------------
                     *** *** ****** ****** **************************

NARP rat sequ        GAGCCTCTCCACCCCTCCTGTAAATGCTAGTGCAACCCAGCCCTGCCTGTCATTTTGGAT
mouse narp nptx2seq  ------------------------------------------------------------

NARP rat sequ        CCTTAGTGTCTCGTGTGTGCTTCCCGTCTGTCCCCTTTGATGGCTGTGTGGTCATCCTAC
mouse narp nptx2seq  ------------------------------------------------------------
```

Figure 3C

```
NARP rat sequ          CGGGGTGGCCTGGGTCCCTTGTGTGTGTAGCACATCCCTGCTTTTGACTGAACACAGTGC
mouse narp nptx2seq    ------------------------------------------------------------

NARP rat sequ          ACAGAAGCTACCCGCCCCTGAAACAGGGTCTCTCCCTCAGTGTCATGTGCACTCTGGTCT
mouse narp nptx2seq    ------------------------------------------------------------

NARP rat sequ          CTCCCTCTGAGGGGACTGCAGCTGCTGGAGGGCCACGTGCCCAGACAGTCCCCAGCATCC
mouse narp nptx2seq    ------------------------------------------------------------

NARP rat sequ          CCAAAGCAGACCCTCCGCCATGGAGAAAGTCCCCCACAGCTTCCCCACCCTCTGTCCACC
mouse narp nptx2seq    ------------------------------------------------------------

NARP rat sequ          TCTCAGACCCCACGCTTCTAAGGACCATTGCTGGGTTGGCTTTCAAAAGCTGCTGCTCTC
mouse narp nptx2seq    ------------------------------------------------------------

NARP rat sequ          ATCTGGTGCCAAAAGTTCATTTGCAGCTTCTACACCGTTCTGTGTGGTTTGGGGATTGAC
mouse narp nptx2seq    --CTCGTGCC--------------------------------------------------
                       **  *****

NARP rat sequ          TTTATTCCCCCACAAAAGAGGAACAGCCATTAGAAGCCAGCCTCCCCTCCTTTTGATGCT
mouse narp nptx2seq    ------------------------------------------------------------

NARP rat sequ          CAGCCCACTGTGAAGAGTGAGCTTGCTTGTAAGCCACATTGGTTTCTGTGAGCATCTGAC
mouse narp nptx2seq    ------------------------------------------------------------

NARP rat sequ          TCTCCCCCGTCCAGTATTTTCCCCGGAACTGGAGATTCGAGTGCCATTCGGCTGCTACCT
mouse narp nptx2seq    ------------------------------------------------------------

NARP rat sequ          GCTTAGTGACTCCAGGCTGCATCATGTATCATAATTTATTTTAAAGACAAAGTGATTCAG
mouse narp nptx2seq    ------------------------------------------------------------

NARP rat sequ          TGGGGAAATTTATAAAGCTATAAATATTATATATTTTATTTTTCATACATGTTTAAAGTG
mouse narp nptx2seq    ------------------------------------------------------------

NARP rat sequ          CGGATCCATGGATGTTCCATTTGTAGGACCAGCTTGACGTGCCCATCCTGACATTGTATG
mouse narp nptx2seq    ------------------------------------------------------------

NARP rat sequ          CCACAAGAGCTCTTGTGATGATGGAATTTTGATTAAAGTGCACTGGAAGATGA
mouse narp nptx2seq    ----------------------GAATTC-------------------------
                                             *****
```

Figure 4
Homology comparison of amino-acid sequences of Rat (SEQ ID No.: 4), Mouse (SEQ ID No.: 6), and Human (SEQ ID No.: 2) Narps

CLUSTAL W (1.7) multiple sequence alignment

```
Narp rat prot        MLALLTAGVALAVAAGQAQDNPIPGSRFVCTALPPEAARAGCPLPAMPMQGGALSPEEEL
narp mouse protein   MLALLTVGVALAVAAGRAQDSPIPGSRFVCTALPPEAARAGCPLPAMPMQGGALSPEEEL
nptx2human protein   MLALLAASVALAVAAG-AQDSPAPGSRFVCTALPPEAVHAGCPLPAMPMQGGAQSPEEEL
                     *****  ******* *** * ************** ************** ******

Narp rat prot        RAAVLHWRETVVQQKETLGAQREAIRELTSKLARCEGLAGGKARGTGATGKDTMGDLPRD
narp mouse protein   RAAVLQLRETVVQQKETLGAQREAIRELTGKLARCEGLAGGKARG---TGKDTMGDLPRD
nptx2human protein   RAAVLQLRETVVQQKETLGAQREAIRELTGKLARCEGLAGGKARGAGATGKDTMGDLPRD
                     *****  **********************  *************    ************

Narp rat prot        PGHVVEQLSRSLQTLKDRLESLELQLHTNASNAGLPSDFREVLQRRLGELERQLLRKVAE
narp mouse protein   PGHVVEQLSRSLQTLKDRLESLELQLRTNVSNAGLPSDFREVLQRRLGELERQLLRKVAE
nptx2human protein   PGHVVEQLSRSLQTLKDRLESLEHQLRANVSNAGLPGDFREVLQQRLGELERQLLRKVAE
                     ********************** ** *  ****** ******* ***************

Narp rat prot        LEDEKSLLHNETSAHRQKTENTLNALLQRVTELERGNSAFKSPDAFKVSLPLRTNYLYGK
narp mouse protein   LEDEKSLLHNETSAHRQKTESTLNALLQRVTELERGNSAFKSPDAFKVSLPLRTNYLYGK
nptx2human protein   LEDEKSLLHNETSAHRQKTESTLNALLQRVTELERGNSAFKSPDAFKVSLPLRTNYLYGK
                     ********************  **************************************

Narp rat prot        IKKTLPELYAFTICLWLRSSASPGIGTPFSYAVPGQANEIVLIEWGNNPIELLINDKVAQ
narp mouse protein   IKKTLPELYAFTICLWLRSSASPGIGTPFSYAVPGQANEIVLIEWGNNPIELLINDKVAQ
nptx2human protein   IKKTLPELYAFTICLWLRSSASPGIGTPFSYAVPGQANEIVLIEWGNNPIELLINDKVAQ
                     ************************************************************

Narp rat prot        LPLFVSDGKWHHICITWTTRDGMWEAFQDGEKLGTGENLAPWHPIKPGGVLILGQEQDTV
narp mouse protein   LPLFVSDGKWHHICITWTTRDGMWEAFQDGEKLGTGENLAPWHPIKPGGVLILGQEQDTV
nptx2human protein   LPLFVSDGKWHHICVTWTTRDGMWEAFQDGEKLGTGENLAPWHPIKPGGVLILGQEQDTV
                     ************** *********************************************

Narp rat prot        GGRFDATQAFVGELSQFNIWDRVLRAQEIINIANCSTNMPGNIIPWVDNNVDVFGGASKW
narp mouse protein   GGRFDATQAFVGELSQFNIWDRVLRAQEIINIANCSTNMPGNIIPWVDNNVDVFGGASKW
nptx2human protein   GGRFDATQAFVGELSQFNIWDRVLRAQEIVNIANCSTNMPGNIIPWVDNNVDVFGGASKW
                     ***************************** ******************************

Narp rat prot        PVETCEERLLDL
narp mouse protein   PVETCEERLLDL
nptx2human protein   PVETCEERLLDL
                     ************
```

Figure 5
Amino acid sequence of gamma-taipoxin (SEQ ID No.: 7)

```
  1  selpqpsidf eqfsnmiqct ipcgseclay mdygcycgpg gsgtpiddld rcckthdecy
 61  aeagklsack svlsepnndt ysyecnegql tcnddndeck aficncdrta vtcfagapyn
121  ddlynigmie chk
```

METHODS OF PREVENTING OR TREATING BRAIN ISCHEMIA OR BRAIN INJURY

This application claims the benefit of U.S. Provisional Application No. 60/359,061, filed Feb. 21, 2002.

FIELD OF THE INVENTION

The present invention relates to use of a Narp inhibitor, in order to promote and enhance recovery from ischemic events, particularly ischemia of the central nervous system, as well as for preventing or diminishing chronic degenerative changes to the central nervous system.

BACKGROUND OF THE INVENTION

Efficient synaptic transmission requires the enrichment and specific localization of receptors on the postsynaptic membranes apposed to the transmitter release sites. In the central nervous system (CNS), ionotropic glutamate receptors are the major excitatory neurotransmitter receptors and are divided into three broad classes, termed AMPA-, NMDA-, and kainate-type receptors, on the basis of molecular and pharmacological criteria. The predominant charge carrier during routine fast excitatory synaptic transmission is the AMPA-type receptor. Functional AMPA receptors are constructed from subunits termed glutamate receptors subunits 1–4 ($GluR_1$–$GluR_4$).

The correlation between various neurological diseases and the structural organization of the AMPA receptor has been the focus of many recent studies. Furthermore, the role of certain growth factors in the regulation of this receptor type has been postulated. For example, O'Brien et al (Neuron, 23, 193, 1999) disclosed that Narp (neural activity-regulated pentraxin) could induce clustering of AMPA receptors. The Narp polypeptide, also called neuronal pentraxin II (NP2) was originally cloned by Tsui et al (J. Neurosci. 16, 2463, 1996) as a novel immediate-early gene (IEG) induced by seizure in rat hippocampus. NARP has been independently identified as the guinea pig sperm acrosome protein p50/apexin (Noland, T. D. et al. (1994) *J. Biol. Chem.* 269, 32607; Reid, M. S., and Blobel, C. P. (1994) *J Biol. Chem.* 269, 32619). O'Brien further provided evidence that Narp may form multimers that subsequently act directly on the AMPA receptor, specifically the $GluR_{1-3}$ subunits, inducing their clustering. Narp appears to derive from both pre- and post synaptic sources. Taken together, these data suggest that Narp may function to facilitate the formation of new excitatory synapses. Since Narp is an Immediate Early Gene (IEG) regulated by synaptic activity, its dynamic expression provides a novel mechanism for activity-dependent synaptogenesis and synaptic plasticity.

U.S. Pat. No. 5,762,552 discloses purified Narp polypeptide, including its amino acid sequence, while WO 97/39133 also provides the polynucleotide encoding the Narp polypeptide, the expression vector containing the above polynucleotides sequence, and a host cell transformed with this vector. Based on the fact that Narp is useful for induction of dendritic neurite outgrowth as well as promotion of neural migration, this patent discloses a method for treating a patient having neuronal disorders, utilizing administration of Narp to the patient.

EP 1,101,820A1 discloses the nucleic acid sequences encoding both human neuronal pentraxin receptor (NPR) and pentraxin I (NP1), and the application is directed to pentraxin I. It only briefly mentions pentraxin II, which is Narp.

WO 00/75661 provides a method for identifying compounds that affect the formation of AMPA receptors into aggregates. WO 00/75661 discloses methods for treating a patient having disorders associated with either an increase or a decrease in the function/expression of Narp, by administering to the patient agents that augment or inhibit Narp function/expression, respectively. WO 00/75661 discloses stimulation of NARP expression or activity for treatment of neuronal cell disorders including stroke or brain or spine cord injury damage including ischemic injury.

Ischemia of the Brain

Brain injury such as trauma and stroke are among the leading causes of mortality and disability in the western world.

Traumatic brain injury (TBI) is one of the most serious reasons for hospital admission and disability in modern society. Clinical experience, suggests that TBI may be classified into primary damage occurring immediately after injury, and secondary damage, which occurs during several days post injury. Current therapy of TBI is either surgical or else mainly symptomatic.

Cerebrovascular diseases occur predominately in the middle and late years of life. They cause approximately 200,000 deaths in the United States each year as well as considerable neurologic disability. The incidence of stroke increases with age and affects many elderly people, a rapidly growing segment of the population. These diseases cause either ischemia-infarction or intracranial hemorrhage.

Stroke is an acute neurologic injury occurring as a result of interrupted blood supply, resulting in an insult to the brain. Most cerebrovascular diseases present as the abrupt onset of focal neurologic deficit. The deficit may remain fixed, it may improve or progressively worsen, leading usually to irreversible neuronal damage at the core of the ischemic focus, whereas neuronal dysfunction in the penumbra may be treatable and or reversible. Prolonged periods of ischemia result in frank tissue necrosis. Cerebral edema follows and progresses over the subsequent 2 to 4 days. If the region of the infarction is large, the edema may produce considerable mass effect with all of its attendant consequences.

Neuroprotective drugs are being developed in an effort to rescue neurons in the penumbra from dying, though as yet none has been proven efficacious.

Damage to neuronal tissue can lead to severe disability and death. The extent of the damage is primarily affected by the location and extent of the injured tissue. Endogenous cascades activated in response to the acute insult play a role in the functional outcome. Efforts to minimize, limit and/or reverse the damage have the great potential of alleviating the clinical consequences.

Taipoxin

Taipoxin is a presynaptic toxin contained in the venom of the Australian taipan snake (*Oxyuranus s. scutellatus*). Fohlman J, (1976) Eur J Biochem 68 457–69. The intact complex molecule of taipoxin is composed of α, β and gamma (γ) subunits. Gamma-taipoxin is composed of 133 amino acids and has a molecular weight of 14.6 Kda. It is the only subunit of taipoxin which is N-glycosylated and sialyzed. Taipoxin is known to bind Narp; in fact, Narp was first purified on an affinity column of taipoxin (Kirkpatrick et al (2000) Biochemical Interactions of the Neuronal Pentraxins. *The Journal of Biological Chemistry*, 275, 23: 17786–17792), and identified through its interaction with taipoxin. In addition, it has been suggested that Narp and Narp receptor (NPR) participate in the internalization pathway of taipoxin into synapses (Dodds et al., Neuronal Pentraxin Receptor, a novel Putative Integral Membrane Pentraxin that Interacts with Neuronal Pentraxin I and II and Taipoxin-associated Calcium-binding Protein 49. The *Journal of Biological Chemistry* 272 (34) : 21488–21494, 1997) WO 01/63293 speaks of a screening method for agents effective for the treatment of schizophrenia, based, inter alia, on the susceptibility of cells exposed to Neural pentraxin I mediated activity to taipoxin. U.S. Pat. No. 4,341,762 concerns the possibility of using combinations of different types of toxins (among them taipoxin) isolated from snake venoms for treatment of neurological and related disorders. Of the 3 separate subunits of taipoxin, the αsubunit was found to be the most toxic (LD 50=300 ug/Kg—European Journal of Biochemistry (1979) 94, 531–540), while evidence of the toxicity of the γ subunit varies (from non-toxic to moderately toxic). The toxicity of the full taipoxin is 2 ug/Kg. The toxicity of α or α+β subunits is highly increased by addition of γ, suggesting that γ is involved in interaction with specific proteins on cell surface. The interaction possibly includes the carbohydrate moiety of γ subunit. The β subunit (β1 and β2) was found to be non-toxic and mitogenic (Lipps (2000) Toxicon 38 1845–1854), and has been proposed as a growth cell factor and for the treatment of wounds (U.S. Pat. Nos. 6,316,602 and 6,307,031).

U.S. Pat. No 6,316,602 relates to the use of beta-taipoxin as a cell-growth factor. This patent is directed primarily to methods of separating beta-taipoxin from the other subunits.

PCT publication No. WO 01/63293 is directed to identification of a long list of proteins and protein isoforms, and the use of these proteins and nucleic acids for screening, diagnosis and therapy of Schizophrenia. A screening method for treating schizophrenia which employs Pentraxin I in order to cause neuronal cells to be susceptible to taipoxin activity is disclosed.

None of the above publications teach or suggest inhibiting Narp in the context of ischemia, and certainly none of the above publications disclose beneficial effects of inhibiting Narp by the gamma subunit of taipoxin in connection with stroke, TBI or other ischemic conditions.

SUMMARY OF THE INVENTION

The present invention provides compositions and methods for alleviation or reduction of the symptoms and signs associated with damaged neuronal tissues whether resulting from tissue trauma, or from chronic degenerative changes. It is an object of the present invention to provide pharmaceutical compositions to reduce or even to completely diminish tissue damage or degeneration due to acute injury to the CNS as described or due to other insults. It is a further object of the present invention to provide methods leading to functional improvement after traumatic ischemic events, including but not limited to traumatic brain injury (TBI) or cerebral stroke. These effects will be achieved by administering an agent that interacts with Narp molecules, and consequently prevents the effect of Narp on AMPA type glutamate receptors.

The preferred methods, materials, and examples that will now be described are illustrative only and are not intended to be limiting; materials and methods similar or equivalent to those described herein can be used in practice or testing of the invention. Other features and advantages of the invention will be apparent from the following detailed description, and from the claims.

DETAILED DESCRIPTION OF THE INVENTION

The present invention provides polypeptides, compositions and methods for alleviation or reduction of the symptoms and signs associated with damaged neuronal tissues whether resulting from tissue trauma, or from chronic degenerative changes. It is an object of the present invention to provide pharmaceutical compositions to reduce or even to completely diminish tissue damage or degeneration. It is a further object of the present invention to provide methods leading to functional improvement after traumatic ischemic events. These effects will be achieved by administering an agent that interacts with Narp molecules, and consequently prevents the effect of Narp.

Narp (also termed neuronal activity regulated pentraxin or neuronal pentraxin II) is a secreted protein the messenger RNA (mRNA) of which is transcribed from an immediate-early gene (IEG) that is rapidly induced in neurons of the hippocampus and cortex by physiological synaptic activity. It has homology to members of the pentraxin family of secreted lectins that include C-reactive protein (CRP) and serum amyloid P (SAP) component. Narp is characterized by a cyclic pentameric structure and radial symmetry. The five identical 24-kDa protomers consist of 206 amino acids, and are noncovalently linked. Given that Narp binds to GluR1 AMPA receptor subunit in a calcium dependent manner, and that its suggested functions are neurite-outgrowth promoting activity (role in excitatory synaptogenesis) and extracellular aggregating factor for AMPA receptors, targeting against Narp may decrease the "excitotoxic" damage mediated by AMPA receptors at the early stages of the ischemic event.

The present invention is based, inlet alia, on the finding by the inventors that in animals which were subjected to middle cerebral artery occlusion (MCAO), an ischemia (stroke) model, the Narp RNA level was significantly upregulated (as compared to controls) following the onset of the ischemic event.

The present invention utilizes a polypeptide, antibody, or a small chemical compound that binds Narp, thus preventing Narp biological activity.

According to a preferred embodiment of the invention, an antibody directed to a neural activity-regulated pentraxin peptide or its immunoreactive fragments is provided.

According to another preferred embodiment of the invention, a polypeptide which binds to a neural activity-regulated pentraxin peptide or fragments thereof is provided.

According to another preferred embodiment of the invention, a small chemical compound which binds to a neural activity-regulated pentraxin polypeptide or fragments thereof is provided.

The term "Narp", as used herein, refers to the Narp (neural activity-regulated pentraxin) polypeptide and is understood to include "neuronal activated pentraxin" (or pentaxin), "pentraxin II" "pentaxin II", and "NP2", derived from any organism, preferably man or mice, and homologs thereof having similar biological activity, preferably having 70%, 80%, 90% or even 95% homology to the Narp polypeptide. Polypeptides encoded by nucleic acid sequences which bind to the Narp gene under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term.

By "biological effect of Narp" or "Narp biological activity" is meant the effect of Narp on AMPA type glutamate receptors, which may be direct or indirect, and includes, without being bound by theory, Neurite-outgrowth promoting activity, and a function as an extracellular aggregating factor for AMPA receptors, which includes an inhibitory effect wherein Narp causes clustering of AMPA receptors on the surface of a cell. The glutamate receptors are preferably on the surface of neuronal cells; the indirect effect includes, but is not limited to, Narp binding to or having an effect on one of several molecules which are involved in a signal transduction cascade resulting in an effect on AMPA type glutamate receptors.

By "Narp inhibitor" is meant any molecule, whether a polypeptide, antibody, or small chemical compound, that prevents or reduces the biological effect of Narp, as recited above. Narp inhibitor may also be an inhibitor of the Narp promoter such as inter alia, antisense RNA molecule, dominant negative peptide (see, for example, O'Brien et al., Synaptically Targeted Narp Plays an Essential Role in the Aggregation of AMPA Receptors at Excitatory Synapses in Cultures Spinal Neurons, *Journal of Neuroscience* 22(11): 4487–4498, 2002, which discloses Narp dominant negative mutants that inhibit Narp activity). A preferred Narp inhibitor is gamma-taipoxin.

By the term "antibody" as used in the present invention is meant both poly- and mono-clonal complete antibodies as well as fragments thereof, such as Fab, F(ab')$_2$, and Fv, which are capable of binding the epitope determinant. These antibody fragments retain the ability to selectively bind with its antigen or receptor and are exemplified as follows, inter alia:

(1) Fab, the fragment which contains a monovalent antigen-binding fragment of an antibody molecule can be produced by digestion of whole antibody with the enzyme papain to yield a light chain and a portion of the heavy chain;

(2) (Fab')$_2$, the fragment of the antibody that can be obtained by treating whole antibody with the enzyme pepsin without subsequent reduction; F(ab'$_2$) is a dimer of two Fab fragments held together by two disulfide bonds;

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule.

Details on how to prepare all types of antibodies are provided in Example 8 below.

By the term "epitope" as used in this invention is meant an antigenic determinant on an antigen to which the antibody binds. Epitopic determinants usually consist of chemically active surface groupings of molecules such as amino acids or sugar side chains and usually have specific three dimensional structural characteristics, as well as specific charge characteristics.

By "Polypeptide" is meant a molecule composed of amino acids and the term includes peptides, polypeptides, proteins and peptidomimetics.

The term "Amino acid" refers to a molecule which consists of any one of the 20 naturally occurring amino acids, amino acids which have been chemically modified (see below), or synthetic amino acids.

The terms "chemical compound", "small molecule", "chemical molecule" "small chemical molecule" and "small chemical compound" are used interchangeably herein and are understood to refer to chemical moieties of any particular type which may be synthetically produced or obtained from natural sources and typically have a molecular weight of less than 2000 daltons, more preferably less than 1000 daltons or even less than 600 daltons.

By "homolog/homology", as utilized in the present invention, is meant at least about 70%, preferably at least about 75% homology, advantageously at least about 80% homology, more advantageously at least about 90% homology, even more advantageously at least about 95%, e.g., at least about 97%, about 98%, about 99% or even about 100% homology. The invention also comprehends that these polynucleotides and polypeptides can be used in the same fashion as the herein or aforementioned polynucleotides and polypeptides.

Alternatively or additionally, "homology", with respect to sequences, can refer to the number of positions with identical nucleotides or amino acid residues, divided by the number of nucleotides or amino acid residues in the shorter of the two sequences, wherein alignment of the two sequences can be determined in accordance with the Wilbur and Lipman algorithm ((1983) Proc. Natl. Acad. Sci. USA 80:726), for instance, using a window size of 20 nucleotides, a word length of 4 nucleotides, and a gap penalty of 4, and computer-assisted analysis and interpretation of the sequence data, including alignment can be conveniently performed using commercially available programs (e.g., Intelligenetics™ Suite, Intelligenetics Inc., Calif.). When RNA sequences are said to be similar, or to have a degree of sequence identity or homology with DNA sequences, thymidine (T) in the DNA sequence is considered equal to uracil (U) in the RNA sequence. RNA sequences within the scope of the invention can be derived from DNA sequences or their complements, by substituting thymidine (T) in the DNA sequence with uracil (U).

Additionally or alternatively, amino acid sequence similarity or homology can be determined, for instance, using the BlastP program (Altschul el al., Nucl. Acids Res. 25:3389–3402) and available at NCBI. The following references provide algorithms for comparing the relative identity or homology of amino acid residues of two polypeptides, and additionally, or alternatively, with respect to the foregoing, the teachings in these references can be used for determining percent homology: Smith et al., (1981) Adv. Appl. Math. 2:482–489; Smith et al., (1983) Nucl. Acids Res. 11:2205–2220; Devereux et al., (1984) Nucl. Acids Res. 12:387–395; Feng et al., (1987) J. Molec. Evol. 25:351–360; Higgins et al., (1989) CABIOS 5:151–153; and Thompson et al., (1994) Nucl. Acids Res. 22:4673–4680.

The present invention is based, inter alia, on the observation by the inventors that occlusion of a cerebral artery, which serves as a model for stroke or other ischemic and hypoxic events, induces significant elevation in Narp transcription as determined by the levels of Narp RNA compared to controls, and on the fact that Narp interacts with certain subunits of AMPA receptors, and subsequently causing their clustering.

The present invention discloses for the first time the utility of Narp inhibition and the utilization of anti-Narp antibodies, Narp inhibitors, use of gamma-taipoxin, small molecules, antisense RNAs, or ribozymes for inhibition of Narp function. Thus, without being bound by theory, we suggest that NARP antibody or other peptide Narp inhibitors or small molecule Narp inhibitors prevent the effect of Narp on Glutamate receptors, possibly the clustering of Glutamate receptors, thereby improving clinical and recovery outcome after brain ischemia or tissue trauma.

It is known in the art, that in certain neurological diseases, for example, brain ischemia or stroke, the blood brain barrier (BBB) is relatively open compared to that of a normal subject, thus enabling penetration of even large molecules such as macromolecules, including antibodies into the brain, and subsequently allowing interaction of the latter with Narp at the post synaptic region. Further information on delivery into the brain is provided in Example 6 herein below.

Without being bound by theory, we suggest that the effect of NARP in the clustering of Glutamate receptors in post-synaptic terminals in the brain as well as its up-regulation following stroke are detrimental. We further suggest that inhibition of the interaction between NARP and the glutamate receptors in the post-synaptic terminals may inhibit the clusters of AMPA receptors in the synapse and inhibit and/or decrease AMPA receptor driven excitotoxicity.

Without being bound by theory, other inhibitors of Narp, apart from gamma taipoxin or anti-Narp antibody, may inhibit (prevent) the effect of Narp on Glutamate receptors. Such inhibitors are inter alia polypeptides capable of inhibiting the effect of NARP (both dominant negative peptides and/or extracellular polypeptides that inhibit the clustering-see, for example, Mi et al., Differing Mechanisms for Glutamate Receptor Aggregation on Dendritic Spines and Shafts in Cultures Hippocampal Neurons. *The Journal of Neuroscience*, 22(17): 7606–7616, 2002) and antisense oligonucleotides such as peptide antagonists, synthetic small molecule antagonists, antisense RNAs, or ribozymes.

The present approach has several distinct advantages over any hitherto available or suggested therapies, including a longer therapeutic effect while preserving the favorable or beneficial effects.

One aspect of this invention provides for a polypeptide that binds to Narp. This polypeptide may be, but is not limited to, an antibody or a portion of a toxin.

Binding of said polypeptide to Narp may occur through a specific binding site or epitope. This binding site is characterized by the fact that it confers to Narp the possibility of executing any of the activities attributed to Narp, including but not limited to neurite-outgrowth promoting activity and function as an extracellular aggregating factor for AMPA receptors. This binding site is further characterized by the fact that binding of the polypeptide of the invention to Narp through this binding site prevents or reduces the biological activity of Narp, including but not limited to Neurite-outgrowth promoting activity and function as an Extracellular aggregating factor for AMPA receptors.

In one embodiment of this invention, the claimed polypeptide is an antibody that inhibits the binding of a murine antibody to Narp, preferably through the same binding site. This inhibition may be tested by methods known to those skilled in the art.

Another aspect of this invention provides for a pharmaceutical composition comprising a Narp inhibitor, preferably a polypeptide, preferably an antibody or a portion of a toxin, preferably taipoxin. In one embodiment of this invention, this pharmaceutical composition is used for alleviation or reduction of the symptoms and signs associated with damaged neuronal tissues whether resulting from tissue trauma, or from chronic degenerative changes.

The Narp inhibitor may cause inhibition of Narp biological activity through several pathways, preferably through binding. Bound Narp may cease to possess Narp activity due to inactivation of a site or an epitope which is crucial to Narp activity (as is possible, for example, in the case of an inhibitor which is a small chemical compound or a portion of a toxin), or due to a spatial interference caused by the bound inhibitor (as is possible for example in the case of an antibody or a portion of a toxin). As a result of binding of the Narp inhibitor to Narp, Narp may no longer possess the possibility of Narp biological activity, which may include, but is not limited to Neurite-outgrowth promoting activity, and a function as an extracellular aggregating factor for AMPA receptors (which includes an inhibitory effect wherein Narp causes clustering of AMPA receptors on the surface of a cell). This prevention of Narp biological activity may aid in alleviation or reduction of the symptoms and signs associated with damaged neuronal tissues whether resulting from tissue trauma, or from chronic degenerative changes.

By "portion of a toxin" is meant a complete subunit or fragment thereof, having the capacity to bind Narp, preferably derived from the toxin taipoxin, most preferably from gamma-taipoxin.

In one aspect of the claimed invention, a portion of a toxin is used in a pharmaceutical composition comprising as an active ingredient a Narp inhibitor (said portion of a toxin) further comprising a pharmaceutically acceptable diluent or carrier. Preferably, said toxin is taipoxin.

A preferred embodiment of this invention is the usage of gamma-taipoxin, or a fragment thereof, as a Narp inhibitor in a pharmaceutical composition comprising as an active ingredient a Narp inhibitor further comprising a pharmaceutically acceptable diluent or carrier, for alleviation or reduction of the symptoms and signs associated with neuronal damage. Gamma-taipoxin was found to be non-toxic by the inventors of the present invention, as detailed below in Example 3. The pharmaceutical composition described in this invention may further contain a diluent or carrier.

The term "gamma-taipoxin" as used herein refers to the gamma subunit of the taipoxin polypeptide, fragments thereof retaining binding activity, and homologs thereof, preferably having at least 70%, more preferably at least 80%, even more preferable at least 90% or 95% homology thereto. This term is understood to encompass polypeptides resulting from minor alterations in the gamma-taipoxin coding sequence, such as, inter alia, point mutations, deletions and insertions which may cause a difference in a few amino acids between the resultant polypeptide and the naturally occurring gamma-taipoxin. Polypeptides encoded by nucleic acid sequences which bind to the gamma-taipoxin coding sequence or genomic sequence under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term. Chemically modified gamma-taipoxin or chemically modified fragments of gamma-taipoxin are also included in the term, so long as the binding activity is retained. The polypeptide sequence of gamma-taipoxin is depicted in FIG. 5 (SEQ ID No: 7). Particular fragments of the gamma-taipoxin polypeptide include amino acids 1–20, 21–40, 41–60, 61–80, 81–100, 101–120 and 121–133 of SEQ ID No: 7. Further particular fragments of the gamma-taipoxin polypeptide include amino acids 10–30, 31–50, 51–70, 71–90, 91–110 and 111–133 of SEQ ID No: 7.

The term "binding activity" as used herein in connection with gamma-taipoxin, refers to the ability of gamma-taipoxin to bind to Narp.

A preferred embodiment of the present invention concerns a method for alleviating or reducing damage to the central nervous system in a patient who has suffered an injury to the central nervous system, comprising administering to the patient a pharmaceutical composition comprising as an active ingredient a Narp inhibitor further comprising a pharmaceutically acceptable diluent or carrier, in a sufficient dosage to alleviate or reduce the damage Another preferred embodiment of the present invention concerns a method for promoting or enhancing recovery in a patient who has suffered an injury to the central nervous system, the method comprising administering to the patient a pharmaceutical composition comprising as an active ingredient a Narp inhibitor further comprising a pharmaceutically acceptable diluent or carrier, in a sufficient dosage to promote or enhance the recovery.

In one aspect of this invention, the injury to the central nervous system which said pharmaceutical composition is aimed at alleviating or reducing, or from which said pharmaceutical composition is aiming to promote or enhance recovery, is an ischemic episode, which may be, but is not limited to, a global or focal cerebral episode.

By "ischemic episode" is meant any circumstance that results in a deficient supply of blood to a tissue. Cerebral ischemic episodes result from a deficiency in the blood supply to the brain. The spinal cord, which is also part of the central nervous system, is equally susceptible to ischemia resulting from diminished blood flow. An ischemic episode may be caused by hypertension, hypertensive cerebral vascular disease, rupture of aneurysm, a constriction or obstruction of a blood vessel- as occurs in the case of a thrombus or embolus, angioma, blood dyscrasias, any form of compromised cardiac function including cardiac arrest or failure, systemic hypotension, cardiac arrest, cardiogenic shock, septic shock, spinal cord trauma, head trauma, seizure, bleeding from a tumor, or other blood loss. It is expected that the invention will also be useful for treating injuries to the central nervous system that are caused by mechanical forces, such as a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracarnial hematoma or edema). Similarly, traumatic constriction or compression can arise from the presence of a mass of abnormal tissue, such as a metastatic or primary tumor.

By "focal ischemia" as used herein in reference to the central nervous system, is meant the condition that results from the blockage of a single artery that supply blood to the brain or spinal cord, resulting in the death of all cellular elements (pan-necrosis) in the territory supplied by that artery.

By "global ischemia" as used herein in reference to the central nervous system, is meant the condition that results from general diminution of blood flow to the entire brain, forebrain, or spinal cord, which causes the death of neurons in selectively vulnerable regions throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension.

In another aspect of this invention, an additional pharmaceutically effective compound is administered in conjunction with the aforementioned pharmaceutical composition.

By "in conjunction with" is meant that the additional pharmaceutically effective compound is administered prior to, at the same time as, or subsequent to administration of Narp inhibitor.

One embodiment of the claimed invention provides for the preparation of a medicament for the treatment of a patient who has suffered an injury to the central nervous system, using a Narp inhibitor. The Narp inhibitor can be any one of those described herein, and is preferably a polypeptide.

The treatment regimen according to the invention is carried out, in terms of administration mode, timing of the administration, and dosage, so that the functional recovery of the patient from the adverse consequences of the ischemic events or central nervous system injury is improved; i.e., the patient's motor skills (e.g., posture, balance, grasp, or gait), cognitive skills, speech, and/or sensory perception (including visual ability, taste, olfaction, and proprioception) improve as a result of antibody administration according to the invention.

Administration of the antibody or polypeptide or small chemical compound according to the invention can be carried out by any known route of administration, including intravenously, intra-arteially, subcutaneously, or intracerebrally. Using specialized formulations, particularly in the case of active fragments of the anti-Narp antibodies, it may also be possible to administer these orally or via inhalation. Suitable doses and treatment regimens for administering antibodies to an individual in need thereof are discussed in detail below.

The invention can be used to treat the adverse consequences of central nervous system injuries that result from any of a variety of conditions. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from tumor, or other blood loss.

Where the ischemia is associated with stroke, it can be either global or focal ischemia, as defined below. It is believed that the administration of an antibody according to the invention is effective, even though administration occurs a significant amount of time following the injury.

A preferred embodiment of the present invention concerns a pharmaceutical composition comprising gamma-taipoxin and a pharmaceutically acceptable carrier.

In an additional embodiment, a composition comprising gamma-taipoxin in an amount effective to treat an injury to the nervous system and a carrier is provided. The carrier may be a pharmaceutically acceptable carrier; further, the composition may be used to treat a patient who has suffered an injury to the central nervous system, such as an ischemic episode, which may be global or focal, or a stroke, by administering- the pharmaceutical composition in a dose sufficient to promote recovery and thereby treat the patient. The administration of the pharmaceutical composition may be periodical. By "periodical" in the context of the administration of a pharmaceutical composition and as used herein is meant administering the pharmaceutical composition in fixed intervals, preferably at fixed times. Such intervals may range from once an hour or every few hours, to once a day, or once every few days or even once a week. More information on dosage and administration regimens is provided in Example 5 below.

An additional embodiment of the present invention concerns the use of gamma-taipoxin in the preparation of a medicament, which may be used for treating a patient who has suffered an injury to the central nervous system, such as, inter alia, a stroke. Another embodiment of the present invention involves a process of identifying a species that modulates binding between Narp and gamma-taipoxin, comprising the steps of:
a) contacting Narp with gamma-taipoxin under binding conditions;
b) contacting Narp, gamma-taipoxin and a species to be tested under the conditions of step a); and
c) comparing the level of binding between Narp and gamma-taipoxin in step a to the level of binding between Narp and gamma-taipoxin in step b), wherein a change in the level of binding is indicative of the ability of the species to modulate the binding between Narp and gamma-taipoxin.

The so identified species may enhance the binding between Narp and gamma-taipoxin.

In general, the term "species" encompasses, inter alia, small chemical molecules, antibodies, antisense oligonucleotides, antisense DNA or RNA molecules, proteins, polypeptides and peptides including peptido-mimetics, expression vectors, lipids, carbohydrates and any other molecule capable of interacting with a naturally occurring molecule.

In an additional embodiment, the present invention provides for a process of identifying a species that possesses the binding activity of gamma-taipoxin comprising the steps of:
a) contacting Narp with gamma-taipoxin under binding conditions;
b) contacting Narp, gamma-taipoxin and a species to be tested under the conditions of step a); and
c) comparing the level of binding between Narp and gamma-taipoxin in step a to the level of binding between Narp and gamma-taipoxin in step b), wherein a lower level of binding between Narp and gamma-taipoxin in step b) (i.e., a decrease in the binding in the presence of the species as compared to the binding in the absence of the species) is indicative of the species possessing gamma-taipoxin-like binding activity.

An additional aspect of the present invention comprises a process of identifying a species that possesses the binding activity of gamma-taipoxin comprising the steps of:
a) contacting cells expressing Narp with a species to be tested;
b) contacting cells lacking normal Narp expression with the species of step a); and
c) assaying for the presence of the species within the cells of step a) and step b), wherein a higher level of the species in the cells of step a) as compared to the level of the species in the cells of step b) is indicative of the species possessing gamma-taipoxin-like binding activity.

In an additional aspect, the present invention provides for a process of identifying a species that possesses the binding activity of gamma-taipoxin comprising the steps of:
a) contacting cells expressing Narp with a species to be tested under binding conditions;
b) contacting cells expressing Narp with gamma-taipoxin and a species to be tested under the conditions of step a) and
c) assaying for the presence of the species within the cells of step a) and step b), wherein a lower level of the species in the cells of step b) as compared to the level of the species in the cells of step a) is indicative of the species possessing gamma-taipoxin-like binding activity.

An additional embodiment of the present invention concerns a process of identifying a species that possesses the binding activity of gamma-taipoxin comprising the steps of:
a) contacting cells expressing Narp with gamma-taipoxin under binding conditions;
b) contacting cells expressing Narp with gamma-taipoxin and a species to be tested under the conditions of step a); and
c) assaying for the presence of gamma-taipoxin within the cells of step a) and step b), wherein a lower level of gamma-taipoxin in the cells of step b) is indicative of the species possessing gamma-taipoxin-like binding activity.

The species identified according to any one of the preceding methods may be a chemical compound.

The detection of binding between Narp and gamma-taipoxin may be performed according to methods known in the art; one preferable method is to perform the screening processes of the present invention with an immuno-fluoresent detection system. For further details on screening assays see Example 7 below.

An additional embodiment of the present invention concerns a process of producing an essentially pure non-toxic preparation of gamma-taipoxin comprising the steps of:
a) obtaining crude taipoxin, containing the α, β, and γ subunits;
b) separating the gamma subunit by gel chromatography; and
c) purifying the gamma subunit by performing ion exchange on the preparation resulting from step b.

The methods of the invention have several advantages. First, an antibody, a polypeptide or a small chemical compound can be administered hours, days, or even weeks, following an injury to the central nervous system. This is advantageous because there is no way to anticipate when such an injury will occur. All the events that cause ischemia or trauma, as discussed above, are unpredictable. Second, this therapeutic regimen improves functional performance without adverse side effects.

The term "Conservative substitution" refers to the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gin, Glu); Class IV (His, Arg, Lys); Class V (Ile, Leu, Val, Met); and Class VI (Phe, Tyr, Trp). For example, substitution of an Asp for another class III residue such as Asn, Gin, or Glu, is a conservative substitution.

The term "Non-conservative substitution"—refers to the substitution of an amino acid in one class with an amino acid from another class; for example, substitution of an Ala, a class II residue, with a class III residue such as Asp, Asn, Glu, or Gin.

By "Chemically modified"—when referring to the product of the invention, is meant a product (polypeptide) where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

The term "Expression vector"—refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

The term "Deletion"—is a change in sequence of either nucleotide or amino acid molecule in which one or more nucleotides or amino acid residues, respectively, are absent.

The term "Insertion" or "addition"—is that change in a sequence of a nucleotide or amino acid molecule resulting in the addition of one or more nucleotides or amino acid residues, respectively, as compared to the naturally occurring molecule.

The term "Substitution" refers to the replacement of one or more nucleotides or amino acids by different nucleotides or amino acids, respectively. As regards amino acid sequences the substitution may be conservative or non-conservative.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

BRIEF DESCRIPTION OF THE FIGURES

FIGS. 1A and 1B are the Human Narp open-reading frame (cDNA) and translation to corresponding polypeptide, SEQ ID No: 1 and SEQ ID No: 2 respectively;

FIGS. 2A and 2B are the Rat Narp open-reading frame (cDNA) and translation to corresponding polypeptide, SEQ ID No: 3 and SEQ ID No: 4 respectively;

FIGS. 3A, 3B and 3C are a homology comparison between the nucleotide sequences of Rat, Mouse, and Human Narps; SEQ ID of Rat and Human Narp nucleotide sequences are as above (SEQ ID No: 3 and 1 respectively); SEQ ID No of Mouse nucleotide sequence is SEQ ID No: 5 and the corresponding polypeptide is SEQ ID No: 6.

FIG. 4 is a homology comparison between the amino-acid sequences of Rat, Mouse, and Human Narps, SEQ ID No: 4, 6 and 2 respectively;

FIG. 5 is the amino acid sequence of gamma-taipoxin, SEQ ID No: 7.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988).

Standard organic synthesis protocols known in the art not specifically described herein are generally followed essentially as in *Organic syntheses*: Vol. 1–79, editors vary, J. Wiley, New York, (1941–2003); Gewert et al., *Organic synthesis workbook*, Wiley-VCH, Weinheim (2000); Smith & March, *Advanced Organic Chemistry*, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

Example 1

Identification and Preparation of key Genes Involved in the Stroke Event

As a first step to the novel drug discovery, key genes involved in the stroke event were identified, as provided by the following methods:

Summary of cDNA Micro-array Construction

The polynucleotide encoding Narp was found by: microarray-based differential gene expression, evaluated by both in vivo and in vitro models.

The cDNA microarray was constructed by combining cDNA libraries (Table 1), including a subtraction library, enriched for stroke specific genes. As a result, the Stroke chip consists of low-redundant stroke-specific clones. The microarray contains 10,000 cDNA clones. The libraries printed on the chip were as described in Table 1.

TABLE 1

The design of Stroke chip: Library types and cDNA sources.

| Type of Library | Material | | Time points | | | |
|---|---|---|---|---|---|---|
| | In vivo | In vitro | 3 h | 6 h | 16 h | 24 h |
| Subtraction library (five independent libraries) | [MCAO] – [Sham] [MCAO + FK50 6] – [MCAO] | | +L3 +L5 | +L4 +L6 | | |
| | | Primary neurons: [Hypoxia + FK506] – [Normoxia + FK506] | +L1 | +L1 | +L1 | +L1 |
| SDGI library (pool of 6 conditions) | MCAO MCAO + FK506 Sham + FK506 | | +L7 +L9 +L10 | +L8 | | |
| | | Primary neurons: [Hypoxia] | +L2 | +L2 | +L2 | +L2 |
| | | Primary neurons: [Hypoxia + FK506] | +L11 | | | |

Each library is indicated by L and numbered. Middle cerebral artery occlusion (MCAO) was performed in SD rats and primary neurons are rat cortical primary neurons. Normoxia indicates normal oxygen concentration.

SDGI—Sequence-dependent Gene Identification.

FK506 (tacrolimus) is a known immunosuppressive agent produced by *Streptomyces tsukubaesis*. FK506 possesses neuroprotective activity by delaying or preventing hypoxia-induced death of neuronal cells. In addition, it can cause re-growth of damaged nerve cells. The specific molecular mechanism underlying the neuroprotective activity of FK506 is largely unknown although there are indications for suppression of activities of calcineurin and nitric oxide synthase as well as prevention of stroke induced generation of ceramide and Fas signaling. In the present invention, FK 506 serves for pinpointing genes that are not only regulated by ischemic-induced damage but are also regulated by the addition of FK-506. Differential profiling of gene expression was performed both in vitro and in vivo models of stroke. In vivo, middle cerebral artery occlusion (MCAO) was personnel by electro-coagulation of the middle cerebral artery (MCA) in rats either treated or untreated with FK506 and sham operated rats. The in vitro model was used was rat primary cortical neuron cultures exposed to either normal oxygen concentrations or hypoxia, with or without FK506 treatment. Accordingly, the present invention is directed to inhibitors of NARP polypeptide the expression of which in neural cells is modulated when cells are subjected to neurotoxic stress.

Gene Discovery Techniques

Three different techniques were used to identify genes that are involved in stroke response and/or regulated by FK506 and by these means Narp was identified. The first technique is known as the "Stroke Chip", on which cDNA fragments that correspond to genes that are believed to be stroke specific were imprinted. These clones were obtained from brain tissue of rats subjected to MCAO and from primary neurons treated in vitro under hypoxic conditions. In the production of the Stroke Chip, the cDNA microarray was constructed by combining various types of libraries. An ischemia (stroke) model was created in SD and SHR rats by permanent middle cerebral artery occlusion (MCAO). Control rats of the same strain were subjected to a sham operation (Sham). Half of the rats of each group were given FK506 treatment at 0 hour. Subtraction libraries comprised genes expressed in the MCAO rats but not in the sham operated rats (MCAO-Sham), and those genes expressed in the MCAO rats treated with FK506 (taken at 3 hours and 6 hours after FK506 treatment) but not in the MCAO treated rats (which had not been subjected to MCAO treatment) in the presence of FK506 ([MCAO+FK506]−[MCAO]). Another library included in the Stroke Chip was derived from in vitro treatment of primary neurons from the cerebellum of 7-day rat pups. The cells were subjected to hypoxia (0.5% $O_2$) for 16 hours. The cells under hypoxia and control cells under normal oxygen concentration (non-moxia) were treated with FK506 (100 ng/ml) at 0 hour and the cDNA extracted after 16 hours. A subtraction library was made from the cDNA fragments expressed in the FK506 treated cells under hypoxia but not in the FK506 treated cells under normoxia ([Hypoxia+FK506]−[Normoxia+FK506]). Additional libraries were generated by sequence-dependent gene identification (SDGI). This technique is described in co-assigned PCT application no. PCT/US01/09392. SDGI libraries were prepared from brain tissues of the rats subjected to MCAO, MCAO rats three and six hours after treatment with FK506, and sham operated rats three and six hours after treatment with FK506. SDGI libraries were prepared from primary neurons that were subjected to hypoxia for 16 hours in the in vitro experiments and from primary neurons, pretreated with FK506 and subjected to hypoxia for 16 hours.

The chip was used for differential hybridization experiments. Thus, cells, either in vivo or in vitro, were subjected to a developmental, physiological, pharmacological or other cued event that would cause genes to be activated or repressed in response thereto. This gene expression array technology was disclosed, for example in U.S. Pat. No. 5,807,522.

Hybridizations

Twenty two hybridizations were performed according with the following scheme summarized in Table 2.

TABLE 2

Probes used for hybridizations on the Stroke chip:

| Probe ID | Treatment |
|---|---|
| FJ65B | 1.5 hr MCAO – cortex |
| FJ66B | 3 hr MCAO – cortex |
| FJ67B | 6 hr MCAO – cortex |
| FJ68B | 12 hr MCAO – cortex |
| FJ69B | 24 hr MCAO – cortex |
| FJ70B | 48 hr MCAO – cortex |
| FJ71B | 1.5 hr MCAO −+ FK-506 cortex |
| FJ72B | 3 hr MCAO −+ FK-506 cortex |
| FJ73B | 6 hr MCAO −+ FK-506 cortex |
| FJ74B | 1.5 hr MCAO – whole hemisphere |
| FJ75B | 3 hr MCAO – whole hemisphere |
| FJ76B | 6 hr MCAO – whole hemisphere |
| FJ77B | 12 hr MCAO – whole hemisphere |
| FJ78B | 24 hr MCAO – whole hemisphere |
| FJ79B | 48 hr MCAO – whole hemisphere |
| FJ80B | 1.5 hr MCAO −+ FK-506 whole hemisphere |
| FJ81B | 3 hr MCAO −+ FK-506 whole hemisphere |
| FJ82B | 6 hr MCAO −+ FK-506 whole hemisphere |
| FJ83B | Sham 1.5 hrs |
| FJ84B | Sham 3 hrs |
| FJ85B | Sham 6 hrs |
| FJ86B | Sham 48 hrs |

In addition to these probes, a common control probe was added to each hybridization (Probe A) labeled with Cy3. The common control probes were mixtures of poly-A RNA extracted from the whole brain of SD rats. In each hybridization a mixture of Probe A and Probe B was used.

Preparation of Tissues for In Situ Analysis

Coronal sections were prepared from paraffin blocks of sham operated rat brains and brains subjected to MCAO.

To characterize the model, control in situ hybridizations and immunostainings were performed. Sections were hybridized to probes specific to genes known to be affected in stroke such as c-fos and p21. Two types of antibodies were used for the immunostaining: a monoclonal antibody against microtubule associated protein 2 (stains neuronal cell body and dendrites indicating the integrity of neuronal cell cytoskeleton); and polyclonal antibodies to GFAP (glial fibrillary acidic protein); this staining is specific for astrocytes and non myelinating oligodendrocytes and indicates the integrity of glial cell cytoskeleton. Results of these hybridizations were consistent with previously reported results. Thus, suitability of obtained paraffin blocks for in situ hybridization study and suitability of the model for this study were demonstrated.

Summary of the Results

CRP binds to a range of substances such as phosphorylcholine, fibronectin, chromatin, histones, and ribonucleoprotein in a calcium-dependent manner. It is a ligand for specific receptors on phagocytic leukocytes, mediates activation reactions on monocytes and macrophages, and activates complement. Plasma CRP is the classical acute-phase protein, increasing 1,000-fold in response to infection, ischemia, trauma, burns, and inflammatory conditions.

The nucleotide and amino acid sequence of the Human Narp polynucleotide (cDNA) and polypeptide (respectively) are given in FIG. 1 (SEQ ID No.'s 1 and 2 respectively). The nucleotide and amino acid sequence of Rat Narp cDNA are shown in FIG. 2 (SEQ ID No.'s 3 and 4 respectively). The base numbers are indicated on the left margin side. Furthermore, the nucleotide sequence comparison between Rat, Mouse and Human (termed: nptx2) Narp is also presented, in FIG. 3 (SEQ ID No.'s 3, 5 and 1 respectively). A * below the rat sequence line designates homology of mouse and human bases with the rat. A comparison between the predicted amino-acid sequences of Rat, Mouse, and Human Narps are shown in FIG. 4 (SEQ ID No.'s 4, 2 and 6 respectively). The sign * has the same designation as in FIG. 3. The nucleotide and the amino-acid sequences of human Narp have been provided previously in U.S. Pat. No. 6,436,673. The nucleotide and the amino-acid sequences of rat Narp have been provided previously in U.S. Pat. No. 5,767,252.

NARP is selectively enriched at excitatory synapses on neurons from both the hippocampus and spinal cord and overexpression of recombinant NARP increases the number of excitatory but not inhibitory synapses in cultured spinal neurons. Narp has several suggested functions:

1) Neurite outgrowth-promoting activity at a concentration of approximately 40 ng/ml, indicating a potency similar to known peptide growth factors and has been suggested to play a key role in excitatory synaptogenesis.
2) Strongly up-regulated in response to ischemia, secreted, and binds to GluR1 AMPA subunit in a calcium-dependent manner.
3) Extracellular aggregating factor for AMPA receptors similarly to agrin for the the acetylcholine receptors
4) It is not known whether Narp has a CRP-like ability to increase PI3K activity In the hybridizations performed to the stroke chip according to the protocol stated above NARP was found to be upregulated in RNA probes derived from animals subjected to MCAO in both the cortex and the ipsilateral hemisphere. The upregulation was immediate ranging from 1.5 to 24 hours. The peak of the upregulation is between 6 and 12 hours. FK-506 known to have a beneficial effect in stroke models decreases the degree of NARP RNA upregulation by 50%.

There is a slight upregulation of NARP in Sham operated animals at 1.5 and 3 hrs, which returns to normal at 6 hours.

TABLE 3

Hybridization results of Narp

| Probe ID | Regulation | Treatment |
|---|---|---|
| FJ65B | 2.3 | 1.5 hr MCAO – cortex |
| FJ66B | 4.6 | 3 hr MCAO – cortex |
| FJ67B | 3.8 | 6 hr MCAO – cortex |
| FJ68B | 4.1 | 12 hr MCAO – cortex |
| FJ69B | 3.9 | 24 hr MCAO – cortex |
| FJ70B | 1 | 48 hr MCAO – cortex |
| FJ71B | 1.8 | 1.5 hr MCAO –+ FK-506 cortex |
| FJ72B | 2.8 | 3 hr MCAO –+ FK-506 cortex |
| FJ73B | 2.9 | 6 hr MCAO –+ FK-506 cortex |
| FJ74B | 1.6 | 1.5 hr MCAO – whole hemisphere |
| FJ75B | 2.4 | 3 hr MCAO – whole hemisphere |
| FJ76B | 6 | 6 hr MCAO – whole hemisphere |
| FJ77B | 5.1 | 12 hr MCAO – whole hemisphere |
| FJ78B | 3.3 | 24 hr MCAO – whole hemisphere |
| FJ79B | 1.7 | 48 hr MCAO – whole hemisphere |
| FJ80B | 2 | 1.5 hr MCAO –+ FK-506 whole hemisphere |
| FJ81B | 3.4 | 3 hr MCAO –+ FK-506 whole hemisphere |
| FJ82B | 3 | 6 hr MCAO –+ FK-506 whole hemisphere |
| FJ83B | 1.9 | Sham 1.5 hrs |
| FJ84B | 2 | Sham 3 hrs |
| FJ85B | 1 | Sham 6 hrs |
| FJ86B | 1.7 | Sham 48 hrs |

The first column in Table 3 depicts the probe name, the second column indicates the differential behavior and the third the treatment description. The differentials are normalized with respect to the normal controls, for example 5.1 (FJ77) means that with that particular probe the amount of NARP RNA was 5.1 times greater than in the normal control. (A differential is considered significant when it is higher than 1.7)

In Situ Experiments Performed in Coronal Sections of MCAO

The $^{35}$S-labeled probe specific to the NARP gene was hybridized to coronal section of rat brains fixed at different time points (1.5 hr, 3 hr, 6 hr, 12 hr, 24 hr, 48 hr, 72 hr and 96 hr) after permanent middle cerebral artery occlusion (MCAO) or sham operation. Results of this in situ hybridization study revealed upregulation of NARP expression in cortical and subcortical neurons in areas adjacent to the infarct core resulting from MCAO. The elevated expression of NARP was detectable in peri-infarct areas from 1.5 hr to 48 hr of MCAO while at 72 and 96 hr hybridization signal at the side ipsilateral to MCAO returned to the level seen at the contralateral side. The results of the DNA microarray based experiments were confirmed by the in situ hybridization studies.

Example 2

Preparation of Taipoxin

Portions (fragments or subunits) of the toxin taipoxin may be produced via several methods, for example:

1) Synthetically;

Synthetic polypeptides can be made using a commercially available machine, using the known sequence of the taipoxin polypeptide or fragments thereof.

2) Recombinant Methods:

A preferred method of making the taipoxin polypeptides (preferably α, β and γ subunits) is to clone a fragment of the cDNA of the taipoxin gene into an expression vector and culture the cell harboring the vector so as to express the encoded polypeptide, and then purify the resulting polypeptide, all performed using methods known in the art (see Deutscher; Harris and Angal).

The expression vector can include a promoter for controlling transcription of the heterologous material and can be either a constitutive or inducible promoter to allow selective transcription. Enhancers that can be required to obtain necessary transcription levels can optionally be included. The expression vehicle can also include a selection gene.

Vectors can be introduced into cells or tissues by any one of a variety of methods known within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al. (1986).

3) Purification from Natural Sources:

Subunits of the toxin taipoxin can be purified from the venom of *Oxyuranus s. scutellatus*, by fractionation on HPLC using ion exchange column, using a Tris-HCL buffer system, as described in Lipps (2000), *Isolation of subunits, α, β and χ of the complex taipoxin from the venom of Australian taipan snake (Oxyuranus s. scutellatus): characterization of β taipoxin as a potent mitogen*. Toxicon 38: 1845–1854

It will be noted that other polypeptides can be prepared according to the above Example, using the appropriate polypeptide sequence or natural source.

Preparation of Gamma Taipoxin

The purification of the gamma subunit of taipoxin was performed essentially as described in Folhman et al., *Eur. J. Biochem* 1976, 68, 457–69, followed by either one of two independent procedures:

a) Anion Exchange Chromatography.

Purified Taipoxin γ was dissolved in 1 ml 50 mM Na-acetate buffer, pH 4 buffer and applied to QAE-Sepharose fast flow colum, equilibrated with the same buffer The unbound fraction, was collected. The bound fraction was eluted with the gradient 0–1 M NaCl in the same buffer. Fractions, eluted with (0.13–0.25 M NaCl), were collected, dialyzed against $NH_4HCO_3$, and 50 μg aliquots were lyophilized.

b) Cation Exchange Chromatography.

Purified Taipoxin γ was dissolved in 1 ml 50 mM Na-phosphate buffer, pH 7.0, and applied to 1 ml SP-Sepharose fast flow column (Pharmacia), equilibrated with the same buffer. The major fraction was in the unbound fraction. It was collected, dialyzed against $NH_4HCO_3$, and 50 μg aliquots were lyophilized. The bound fraction was eluted with 1 M NaCl in the same buffer.

In further detail, one method of purifying gamma-taipoxin was performed as follows: crude taipoxin, containing α, β, and γ subunits, was purchased from Alomone Labs, Jerusalem. The lyophilized powder of crude taipoxin was dissolved in deionized water, lyophilized, and dissolved in 2 ml 6 M Guanidinium HCl. It was applied to Sephacryl S-200 column, equilibrated with 6 M Guanidinium HCl, and the γ subunit was separated from α and β subunits by gel chromatography (Fohlman, J. et al. (1976) *Eur. J. Biochem.* 68, 457).

The fractions containing the γ subunit were pooled, dialyzed into 50 mM $NH_4HCO_3$, and lyophilized. The lyophilized fraction was redissolved in 6 M Guanidinium HCl and re-applied to Sephacryl S-200 column, equilibrated with 6 M Guanidinium HCl. The re-chromatography was performed in order to remove traces of α and β subunits.

The fractions were then pooled and dialyzed into 50 mM Na-phosphate buffer pH 7.0. The dialyzed fraction was applied to SP-Sepharose fast flow column (1 ml). The γ subunit did not bind to SP-Sepharose in these conditions. The bound material, containing some residual impurities, was eluted with 1 M NaCl in 50 mM Na-phosphate buffer pH 7.0. It did not exceed 1% of the applied material.

The flow-through, containing the γ subunit, was dialyzed into 50 mM $NH_4HCO_3$, and the protein content was spectrophotometrically calculated.

Example 3

Toxicity

The gamma subunit of taipoxin was proven to be non-toxic according to the following procedures:

A) In Vitro Toxicity of Gamma-taipoxin

P19 differentiated neurons were prepared according to protocols known in the art. Two weeks after differentiation, gamma-taipoxin or crude taipoxin are added to the cells and cell viability is subsequently measured using Alamar Blue.

Results

A concentration of 0. ug/ml of taipoxin caused cell death of ~60% of P19 undifferentiated cells and ~80% of P19 differentiated neurons. Under the selected range of concentrations, taipoxin behaves consistently, killing more than 90% of the cells.

A concentration of 1 ug/ml of gamma-taipoxin caused cell death of ~50% of P19 differentiated neurons, while P19 undifferentiated cells were not affected by gamma-taipoxin in the test concentrations ranging from 0.5 ug/ml to 10 ug/ml.

Therefore, taking in account the molar ratio, gamma-taipoxin is several hundred folds less toxic than crude taipoxin in P19 differentiated neurons.

In an additional experiment, different concentrations of gamma-taipoxin or crude taipoxin were added to the cultured cortical neurons (80000 cells/well in 96-well microplate), and after overnight incubation at 37° C. the living cells were detected with Alamar Blue.

Results

The crude taipoxin was toxic in all concentrations tested (the lowest concentration was 62.5 ng/ml). By contrast, the toxicity of gamma-taipoxin was detected only at very high concentrations ($IC_{50}$>5 μg/ml). The lower concentrations of gamma-taipoxin did not exert any toxicity. The toxicity of gamma-taipoxin is <1% of that of the crude taipoxin.

B) In Vivo Toxicity of gamma-taipoxin

Crude taipoxin and gamma-taipoxin were separately administered intraperitoneally (IP-single injection) in mice. Taipoxin was administered at 3 dose levels of 0.5, 1 and 2 ug/Kg (LD50). Gamma-taipoxin was administered at 3 dose levels of 60, 600 and 1000 ug/Kg (½ of the LD50 concentration). An additional group administered physiological saline served as the vehicle control group.

Results

Two animals (out of 5) which received 2 ug/kg taipoxin were euthanized after exhibiting signs of piloerection, severe dyspnea, decreased spontaneous motor activity and emaciation. Clinical signs were confined to the animals which received 2 ug/kg taipoxin. No major gross pathological findings were noted in gamma-taipoxin treated animals or control animals.

Based on the results of the above experiments, dose levels of taipoxin below 0.5 ug/kg, and gamma-taipoxin below 1000 ug/kg may be considered as non-observed adverse effects levels (NOEL). The gamma sub-unit of taipoxin is therefore non-toxic.

Example 4

Experimental models

CNS injury—The potential of the use of anti-Narp antibody or other Narp inhibitor for treating CNS injury is evaluated in animal models. The models represent varying levels of complexity, by comparison of control animals to the antibody-treated animals. The efficacy of such treatment is evaluated in terms of clinical outcome, neurological deficit, dose-response and therapeutic window. Test animals are treated intravenously or subcutanously with anti-Narp antibody or other Narp inhibitor prepared in a suitable buffer. Control animals are treated with buffer only. Models used are as follows.

1. Closed Head Injury (CHI)—Experimental TBI produces a series of events contributing to neurological and neurometabolic cascades, which are related to the degree and extent of behavioral deficits. CHI is induced under anesthesia, while a weight is allowed to free-fall from a prefixed height (Chen et al, J. Neurotrauma 13, 557, 1996) over the exposed skull covering the left hemisphere in the midcoronal plane.
2. Transient middle cerebral artery occlusion (MCAO)—a 90 to 120 minutes transient focal ischemia is performed in adult, male Sprague Dawley rats, 300–370 gr. The method employed is the intraluminal suture MCAO (Longa et al., Stroke, 30, 84, 1989, and Dogan et al., J. Neurochem. 72, 765, 1999). Briefly, under halothane anesthesia, a 3-0-nylon suture material coated with Poly-L-Lysine is inserted into the right internal carotid artery (ICA) through a hole in the external carotid artery. The nylon thread is pushed into the ICA to the right MCA origin (20–23 mm). 90–120 minutes later the thread is pulled off, the animal is closed and allowed to recover.
3. Permanent middle cerebral artery occlusion (MCAO)—occlusion is permanent, unilateral-induced by electrocoagulation of MCA. Both methods lead to focal brain ischemia of the ipsilateral side of the brain cortex leaving the contralateral side intact (control). The left MCA is exposed via a temporal craniectomy, as described for rats by Tamura A.et al., *J Cereb Blood Flow Metab.* 1981; 1:53–60. The MCA and its lenticulostriatal branch are occluded proximally to the medial border of the olfactory tract with microbipolar coagulation. The wound is sutured, and animals returned to their home cage in a room warmed at 26° C. to 28° C. The temperature of the animals is maintained all the time with an automatic thermostat.

Evaluation Process The efficacy of the anti-Narp antibody or other Narp inhibitors is determined by mortality rate, weight gain, infarct volume and by short and long term clinical and neurophysichological outcomes in surviving animals. Infarct volumes are assessed histologically (Knight et al., Stroke, 25, 1252, 1994, and Mintorovitch et al., Magn. Reson. Med. 18, 39, 1991). The staircase test (Montoya et al., J. Neurosci. Methods 36, 219, 1991) or the motor disability scale according to Bederson's method (Bederson et al., Stroke, 17, 472, 1986) are employed to evaluate the functional outcome following MCAO. The animals are followed for different time points, the longest one being two months. At each time point (24h, 1 week, 3, 6, 8 weeks), animals are sacrificed and cardiac perfusion with 4% formaldehyde in PBS is performed. Brains are removed and serial coronal 200 m sections are prepared for processing and paraffin embedding. The sections are stained with suitable dyes such as TCC. The infarct area is measured in these sections using a computerized image analyzer.

Utilization of the anti-Narp antibody or other Narp inhibitor treatment as exemplified in the above animal models provides new possibilities for treatment of human brain injury.

Example 5

Neuroprotective Effects of Gramma-taipoxin in a Rat Stroke Model

The neuroprotective efficacy of gamma-taipoxin was evaluated in rat stroke models of permanent focal cerebral ischemia, as described herein.

Permanent focal ischemia were performed using 9-week old male Sprague-Dawley rats which were purchased from Japan SLC, Inc. (Hamamatsu, Japan). Eleven animals were employed for each treatment group. Lyophilized taipoxin γ prepared as described in Example 2 was dissolved and diluted with phosphate buffered saline. The drug was infused continuously to the lateral ventricular area beginning from 24 hours before to 24 hours after MCAO in the dosage of 0.48, 4.8 or 48 μg/head/day using Alzet osmotic mini pump (ALZA, Calif., USA). The infusion rate was 1 μL/hour. In the control group, the vehicle alone was administered. Focal ischemia was induced by permanent coagulation of the middle cerebral artery. Rats were anesthetized with halothane (4% for induction, 1.5% for maintenance) in a mixture of 70% of nitrous oxide and 30% oxygen during surgery. Under the subtemporal craniotomy, the left MCA was exposed by a microsurgical approach and the MCA was occluded by bipolar electrocoagulation. After occlusion of the MCA, the temporalis muscle and skin were closed in layers and anesthesia was discontinued. Rectal temperature of rats was maintained at 37.0–38.5° C. with a heating-pad during the surgery. Twenty-four hours after MCAO, rats were perfused with saline under pentobarbital anesthesia (50 mg/kg, i.p.) and their brains were removed. The brain was coronally sectioned in 2-mm thickness from +4 to −6 mm from bregma, and then the six consecutive slices were stained with 2% 2,3,5-triphenyltetrazolium chloride (TTC) at 37° C. for 30 minutes. The area of ischemic brain damage and the whole area of cerebrum in 6 sections were calculated by using a computerized image analysis system. The brain damage was expressed as the percentage of the sum of the area of damaged brain to the sum of the whole area of cerebrum and the volume of ischemic brain damage was calculated. Statistical comparison between the vehicle-treated control and the taipoxin γ-treated groups was performed by Dunnett's multiple comparison test. All results are expressed as the mean±S.E.M.

Results

The rats received with i.c.v. infusion of taipoxin γ showed no obvious abnormal behavior during the course of experiments. Permanent occlusion of the left MCA resulted in ischemic brain damage within the territory of the MCA, i.e. in the dorsolatelal cortex and striatum. Volumes of total, cortical and subcortical ischemic brain damage in the vehicle-treated control group were 255.00±15.14, 170.43±13.39 and 84.57±3.81 mm$^3$, respectively. The size of ischemic brain damage is therefore dose-dependent (Table 4). Taipoxin-γ at doses ranging from 0.48 to 48 μg/head/day infused intracerebrally reduced the size of ischemic brain damage dose-dependently, with significant effects at doses of 48 μg/head/day. Taipoxin-γ dramatically reduced damaged area in the cerebral cortex but only minimally affected the striatal infarction. Cortical damage was reduced by 15.9%, 18.9% and 26.6% at the doses of 0.48, 4.8, and 48 μg/head/day, respectively.

TABLE 4

Neuroprotective effect of taipoxin in a focal cerebral ischemia model in rats

| Dosage of taipoxin | Infarction area in the cerebral cortex (%) | Infarction area in the striatum (%) | Infraction area in the total brain (%) |
|---|---|---|---|
| Vehicle | 12.73 ± 1.07 | 5.81 ± 0.28 | 18.55 ± 1.23 |
| 0.48 μg/head/day | 10.70 ± 0.71 | 5.81 ± 0.30 | 16.50 ± 0.87 |
| 4.8 μg/head/day | 10.32 ± 0.98 | 5.21 ± 0.32 | 15.53 ± 0.88 |
| 48 μg/head/day | 9.35 ± 0.77 * | 5.74 ± 0.23 | 15.09 ± 0.88 * |

* $P < 0.05$; statistically significant compared to vehicle-treated control group (by Dunnett's multiple comparison test). Eleven animals were employed for each treatment group.

Example 6

Pharmacology and Drug Delivery

The compound of the present invention is administered and dosed in accordance with good medical practice, taking into account the clinical condition of the individual patient, the disease to be treated, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The treatment generally has a length proportional to the length of the disease process and drug effectiveness and the patient species being treated. It is noted that humans are treated generally longer than the mice or other experimental animals exemplified herein.

The compound of the present invention can be administered by any of the conventional routes of administration. It should be noted that it can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic cosolvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention.

When administering the compound of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques which deliver it orally or intravenously and retain the biological activity are preferred. In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used.

Antibodies are typically administered over several days or weeks. They may be injected intravenously or subcutaneously. Antibodies acting on the central nervous system may be administered in bolus or with infusion all the time that the brain blood barrier is open (usually 24 following brain injury, either stroke or TBI.)

The dose and the route of administration of the antibody may vary, and will be determined by the attending physician in accordance with the medical history. In one representative example, therapeutic antibodies against ICAM-1 were administrated to laboratory animals at a dose of 2 mg/kg over a 3 minute interval, two hours upon middle cerebral artery occlusion followed by a second administration of 1 mg/kg 22 hrs following middle cerebral artery occlusion. (Zhang R. L et al., Stroke, 26: 1438–1443, 1995).

In general, the active dose for humans is in the range of from 1 ng/kg to about 20–100 mg/kg body weight per day, preferably about 0.01 mg to about 2–10 mg/kg body weight per day, in a regimen of one dose per day or twice or three or more times per day for a period of 1–2 weeks or longer, preferably for 24-to 48 hrs or by continuous infusion during a period of 1–2 weeks or longer.

It will be appreciated that the most appropriate administration of the pharmaceutical compositions of the present invention will depend on the type of injury or disease being treated. Thus, the treatment of an acute event will necessitate systemic administration of the active composition comparatively rapidly after induction of the injury. On the other hand, diminution of chronic degenerative damage may necessitate a sustained dosage regimen.

Delivery of Gamma-taipoxin into the Brain

Delivery of compounds into the brain can be accomplished by several methods such as, inter alia, neurosurgical implants, blood-brain barrier disruption, lipid mediated transport, carrier mediated influx or efflux, plasma protein-mediated transport, receptor-mediated transcytosis, absorptive-mediated transcytosis, neuropeptide transport at the blood-brain barrier, and genetically engineering "Trojan horses" for drug targeting. The above methods are performed essentially as described in "*Brain Drug Targeting: the future of brain drug development*", W. M. Pardridge, Cambridge University Press, Cambridge, UK (2001). In particular, delivery of polypeptides such as gamma-taipoxin or fragments thereof can be accomplished by genetically engineering "Trojan horses" for drug targeting such as, for example, peptidomimetic monoclonal antibodies that are ligands for blood-barin barrier endogenous receptors.

Example 7

Screening Assays

The Narp gene may be used in a screening assay for identifying and isolating compounds which inhibit stroke. The compounds to be screened comprise inter alia substances such as small chemical molecules, antibodies, antisense oligonucleotides, antisense DNA or RNA molecules, polypeptides and dominant negative or dominant positive peptides, and expression vectors. (A synthetic antisense oligonucleotide drug can inhibit translation of mRNA encoding the gene product of a gene involved in the stroke event.) Small chemical molecules generally have a molecular weight of less than 2000 daltons, more preferably less than 1000 daltons or even less then 600 daltons.

Many types of screening assays are known to those of ordinary skill in the art. The specific assay which is chosen depends to a great extent on the activity of the candidate gene or the polypeptide expressed thereby. Thus, if it is known that the expression product of a candidate gene has enzymatic activity, then an assay which is based on inhibition (or stimulation) of the enzymatic activity can be used. If, as in the case of Narp, the candidate polypeptide is known to bind to a ligand or other interactor, then the assay can be based on the inhibition of such binding or interaction. When the candidate gene is a known gene, then many of its properties can also be known, and these can be used to determine the best screening assay. If the candidate gene is novel, then some analysis and/or experimentation is appropriate in order to determine the best assay to be used to find inhibitors of the activity of that candidate gene. The analysis can involve a sequence analysis to find domains in the sequence which shed light on its activity.

As is well known in the art, the screening assays can be cell-based or non-cell-based. The cell-based assay is performed using eukaryotic cells such as HeLa cells. One way of running such a cell-based assay uses tetracycline-inducible (Tet-inducible) gene expression. Tet-inducible gene expression is well known in the art; see for example, Hofmann et al, 1996, Proc Natl Acad Sci 93(11):5185–5190.

Tet-inducible retroviruses have been designed incorporating the Self-inactivating (SIN) feature of a 3' Ltr enhancer/promoter retroviral deletion mutant. Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, thus indicating that expression is regulated uniformly within the infected cell population.

If the gene product of the candidate gene phosphorylates with a specific target protein, a specific reporter gene construct can be designed such that phosphorylation of this reporter gene product causes its activation, which can be followed by a color reaction. The candidate gene can be specifically induced, using the Tet-inducible system discussed above, and a comparison of induced versus non-induced genes provides a measure of reporter gene activation.

In a similar indirect assay, a reporter system can be designed that responds to changes in protein-protein interaction of the candidate protein. If the reporter responds to actual interaction with the candidate protein, a color reaction occurs.

One can also measure inhibition or stimulation of reporter gene activity by modulation of its expression levels via the specific candidate promoter or other regulatory elements. A specific promoter or regulatory element controlling the activity of a candidate gene is defined by methods well known in the art. A reporter gene is constructed which is controlled by the specific candidate gene promoter or regulatory elements. The DNA containing the specific promoter or regulatory agent is actually linked to the gene encoding the reporter. Reporter activity depends on specific activation of the promoter or regulatory element. Thus, inhibition or stimulation of the reporter is a direct assay of stimulation/ inhibition of the reporter gene; see, for example, Komarov et al (1999), Science vol 285, 1733–7 and Storz et al (1999) Analytical Biochemistry, 276, 97–104.

Various non-cell-based screening assays are also well within the skill of those of ordinary skill in the art. For example, if enzymatic activity is to be measured, such as if the candidate protein has a kinase activity, the target protein can be defined and specific phosphorylation of the target can be followed. The assay can involve either inhibition of target phosphorylation or stimulation of target phosphorylation, both types of assay being well known in the art; for example see Mohney et al (1998) J. Neuroscience 18, 5285 and Tang et al (1997) J Clin. Invest. 100, 1180 for measurement of kinase activity. Although this is not relevant in cases where there is no known enzymatic activity, there is a possibility that non enzyme proteins interact with an enzyme and regulate its enzymatic activity through protein-protein interaction.

One can also measure in vitro interaction of a candidate polypeptide with interactors. In this screen, the candidate polypeptide is immobilized on beads. An interactor, such as a receptor ligand, is radioactively labeled and added. When it binds to the candidate polypeptide on the bead, the amount of radioactivity carried on the beads (due to interaction with the candidate polypeptide) can be measured. The assay indicates inhibition of the interaction by measuring the amount of radioactivity on the bead.

Any of the screening assays, according to the present invention, can include a step of identifying the chemical compound (as described above) which tests positive in the assay and can also include the further step of producing as a medicament that which has been so identified. It is considered that medicaments comprising such compounds, or chemical analogs or homologs thereof, are part of the present invention. The use of any such compounds identified for prevention or treatment of stroke or other ischemic events, is also considered to be part of the present invention.

A particular screening system in which Narp can be employed is disclosed in O'Brien et al., Synaptically Targeted Narp Plays an Essential Role in the Aggregation of AMPA Receptors at Excitatory Synapses in Cultures Spinal Neurons, *Journal of Neuroscience* 22(11): 4487–4498, 2002, and in PCT application publication No. 97/39133.

Example 8

Preparation of Anti-Narp Antibodies

Antibodies which bind to the Narp polypeptide of the invention may be prepared using an intact Narp polypeptide or fragments containing smaller polypeptides as the immunizing antigen. For example, it may be desirable to produce antibodies that specifically bind to the N- or C-terminal or any other suitable domains of Narp. The polypeptide used to immunize an animal can be derived from translated cDNA or chemical synthesis which can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal.

If desired, polyclonal or monoclonal antibodies can be further purified, for example by binding to and elution from a matrix to which the polypeptide or a peptide to which the antibodies were raised is bound. Those skilled in the art know various techniques common in immunology for purification an/or concentration of polyclonal as well as monoclonal antibodies (Coligan et al, Unit 9, Current Protocols in Immunology, Wiley Interscience, 1994, incorporated by reference). Methods for making antibodies of all types, including fragments, are known in the art (See for example, Harlow and Lane, Antibodies: A Laboratory Manual, Cold Spring Harbor Laboratory, New York (1988) incorporated herein by reference). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR-grafting (EP239,400; PCT publication WO.91/09967; U.S. Pat. Nos. 5,225,539; 5,530,101; and 5,585,089, veneering or resurfacing (EP 592,106; EP 519,596; Padlan, Molecular Immunology 28(4/5):489–498 (1991); Studnicka et al., Protein Engineering 7(6):805–814 (1994); Roguska et al., PNAS 91:969–973 (1994)), and chain shuffling (U.S. Pat. No. 5,565,332).

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,11 1; and, PCT publications WO 98/46645, WO 98/50433, WO 98/24893, WO 98/16654, WO 96/34096, WO 96/33735, and WO 91/10741; each of which is incorporated herein by reference in its entirety.

Additional information regarding all types of antibodies, including humanized antibodies, human antibodies and antibody fragments can be found in WO 01/05998, which is incorporated herein by reference in its entirety.

The invention claimed is:

1. A method of treating a patient who has suffered an injury to the central nervous system, comprising administering to the patient a dose of a pharmaceutical composition consisting essentially of gamma-taipoxin as an active ingredient effective to alleviate the symptoms associated with damaged neuronal tissues, thereby treating the patient, wherein the gamma-taipoxin consists of the amino acid sequence of SEQ ID NO:7.

2. The method of claim 1, wherein the composition is administered periodically.

3. The method of claim 2, wherein the administration is performed daily.

4. The method of claim 2, wherein the administration is performed twice per day.

5. The method of claim 2, wherein the administration is performed three times per day.

6. The method of claim 1, wherein the composition is administered by continuous infusion.

7. The method of claim 1, wherein the injury is an ischemic episode.

8. The method of claim 7, wherein the ischemic episode is a global cerebral episode.

9. The method of claim 7, wherein the ischemic episode is a focal cerebral episode.

10. The method of claim 1, wherein the injury comprises a stroke.

11. The method of claim 1, wherein the concentration of the active ingredient in the pharmaceutical composition ranges from 1 μg/mL to 10 μg/mL.

12. The method of claim 1, wherein the dose of the active ingredient ranges from 60 μg/Kg to 1000 μg/Kg of patient body weight.

13. The method of claim 1, wherein the dose of the active ingredient ranges from 0.48 μg per patient daily to 48 μg per patient daily.

14. The method of claim 1, wherein the dose of the active ingredient ranges from 1 ng/Kg to 100 mg/Kg of patient body weight per day.

15. The method of claim 1, wherein the dose of the active ingredient ranges from 1 ng/Kg to 20 mg/Kg of patient body weight per day.

16. The method of claim 1, wherein the dose of the active ingredient ranges from 0.01 mg/Kg to 20 mg/Kg of patient body weight per day.

17. The method of claim 1, wherein the dose of the active ingredient ranges from 0.01 mg/Kg to 10 mg/Kg of patient body weight per day.

18. The method of claim 1, wherein the dose of the active ingredient ranges from 0.01 mg/Kg to 2 mg/Kg of patient body weight per day.

* * * * *

SEQUENCE LISTING

<160> NUMBER OF SEQ ID NOS: 7

<210> SEQ ID NO 1
<211> LENGTH: 2746
<212> TYPE: DNA
<213> ORGANISM: Homo sapiens

```
<220> FEATURE:
<221> NAME/KEY: CDS
<222> LOCATION: (166)..(1461)

<400> SEQUENCE: 1
agcgcggtgg gtgcggctgt gagacggcag gagacttctg ccccgcggtg cacgcgaccc      60
tcgagacgac agcgcggcta ctgccagcag cgaaggcgcc tcccgcggag cgcccagacg     120
gcgcccgctc gcccatgccg agctgagcgc ggcagcggcg cggg atg ctg gcg ctg     177
                                              Met Leu Ala Leu
                                                1 ctg gcc gcc agc gtg gcg ctc gcc gtg gcc gct ggg gcc cag gac agc     225
Leu Ala Ala Ser Val Ala Leu Ala Val Ala Ala Gly Ala Gln Asp Ser
  5                  10                 15                  20 ccg gcg ccc ggt agc cgc ttc gtg tgc acg gca ctg ccc cca gag gcg     273
Pro Ala Pro Gly Ser Arg Phe Val Cys Thr Ala Leu Pro Pro Glu Ala
                 25                  30                  35 gtg cac gcc ggc tgc ccg ctg ccc gcg atg ccc atg cag ggc ggc gcg     321
Val His Ala Gly Cys Pro Leu Pro Ala Met Pro Met Gln Gly Gly Ala
             40                  45                  50 cag agt ccc gag gag gag ctg agg gcc gcg gtg ctg cag ctg cgc gag     369
Gln Ser Pro Glu Glu Glu Leu Arg Ala Ala Val Leu Gln Leu Arg Glu
         55                  60                  65 acc gtc gtg cag cag aag gag acg ctg ggc gcg cag cgc gag gcc atc     417
Thr Val Val Gln Gln Lys Glu Thr Leu Gly Ala Gln Arg Glu Ala Ile
     70                  75                  80 cgc gag ctc acg ggc aag cta gcg cgc tgc gag ggg ctg gcg ggc ggc     465
Arg Glu Leu Thr Gly Lys Leu Ala Arg Cys Glu Gly Leu Ala Gly Gly
 85                  90                  95                 100 aag gcg cgc ggc gcg ggg gcc acg ggc aag gac act atg ggc gac ctg     513
Lys Ala Arg Gly Ala Gly Ala Thr Gly Lys Asp Thr Met Gly Asp Leu
                105                 110                 115 ccg cgg gac ccc ggc cac gtc gtg gag cag ctc agc cgc tcg ctg cag     561
Pro Arg Asp Pro Gly His Val Val Glu Gln Leu Ser Arg Ser Leu Gln
            120                 125                 130 acc ctc aag gac cgc ctg gag agc ctc gag cac cag ctc aga gca aac     609
Thr Leu Lys Asp Arg Leu Glu Ser Leu Glu His Gln Leu Arg Ala Asn
        135                 140                 145 gtg tcc aat gct ggg ctg ccc ggc gac ttc cgc gag gtg ctc cag cag     657
Val Ser Asn Ala Gly Leu Pro Gly Asp Phe Arg Glu Val Leu Gln Gln
    150                 155                 160 cgg ctg ggg gag ctg gag agg cag ctt ctg cgc aag gtg gca gag ctg     705
Arg Leu Gly Glu Leu Glu Arg Gln Leu Leu Arg Lys Val Ala Glu Leu
165                 170                 175                 180 gag gac gag aag tcc ctg ctg cac aat gag acc tcg gct cac cgg cag     753
Glu Asp Glu Lys Ser Leu Leu His Asn Glu Thr Ser Ala His Arg Gln
                185                 190                 195 aag acc gag agc acc ctg aac gcg ctg ctg cag agg gtc acc gag ctg     801
Lys Thr Glu Ser Thr Leu Asn Ala Leu Leu Gln Arg Val Thr Glu Leu
            200                 205                 210 gag cga ggc aat agc gcc ttt aag tca cca gat gcg ttc aag gtg tcc     849
Glu Arg Gly Asn Ser Ala Phe Lys Ser Pro Asp Ala Phe Lys Val Ser
        215                 220                 225 ctc cca ctc cgc aca aac tac cta tac ggc aag atc aag aag acg ctg     897
Leu Pro Leu Arg Thr Asn Tyr Leu Tyr Gly Lys Ile Lys Lys Thr Leu
    230                 235                 240 cct gag ctg tac gcc ttc acc atc tgc ctg tgg ctg cgg tcc agc gcc     945
Pro Glu Leu Tyr Ala Phe Thr Ile Cys Leu Trp Leu Arg Ser Ser Ala
245                 250                 255                 260 tca cca ggc att ggc acc ccc ttc tcc tat gcg gtg cca ggg cag gcc     993
```

```
Ser Pro Gly Ile Gly Thr Pro Phe Ser Tyr Ala Val Pro Gly Gln Ala
            265                 270                 275
```

| | |
|---|---|
| aac gag atc gtg ctg atc gag tgg ggc aac aac ccc atc gag ctg ctc<br>Asn Glu Ile Val Leu Ile Glu Trp Gly Asn Asn Pro Ile Glu Leu Leu<br>              280                 285              290 | 1041 |
| atc aac gac aag gtt gcg cag ctg ccc ctg ttt gtc agt gac ggc aag<br>Ile Asn Asp Lys Val Ala Gln Leu Pro Leu Phe Val Ser Asp Gly Lys<br>    295                 300               305 | 1089 |
| tgg cac cac atc tgt gtc acc tgg acg aca cgg gat ggc atg tgg gag<br>Trp His His Ile Cys Val Thr Trp Thr Thr Arg Asp Gly Met Trp Glu<br>       310              315              320 | 1137 |
| gca ttc cag gac gga gag aag ctg ggc act ggg gag aac ctg gcc ccc<br>Ala Phe Gln Asp Gly Glu Lys Leu Gly Thr Gly Glu Asn Leu Ala Pro<br>325                 330              335              340 | 1185 |
| tgg cac ccc atc aag ccc ggg ggc gtg ctg atc ctt gga caa gag cag<br>Trp His Pro Ile Lys Pro Gly Gly Val Leu Ile Leu Gly Gln Glu Gln<br>                345              350              355 | 1233 |
| gac acc gtg ggg ggt agg ttt gat gcc act cag gca ttt gtc ggg gag<br>Asp Thr Val Gly Gly Arg Phe Asp Ala Thr Gln Ala Phe Val Gly Glu<br>           360              365              370 | 1281 |
| ctc agc cag ttc aac ata tgg gac cgc gtc ctt cgc gca caa gaa att<br>Leu Ser Gln Phe Asn Ile Trp Asp Arg Val Leu Arg Ala Gln Glu Ile<br>     375                380              385 | 1329 |
| gtc aac atc gcc aac tgc tcc aca aac atg ccg ggc aac atc atc ccg<br>Val Asn Ile Ala Asn Cys Ser Thr Asn Met Pro Gly Asn Ile Ile Pro<br>    390               395              400 | 1377 |
| tgg gtg gac aat aac gtc gat gtg ttc gga ggg gcc tcc aag tgg ccc<br>Trp Val Asp Asn Asn Val Asp Val Phe Gly Gly Ala Ser Lys Trp Pro<br>405                 410              415              420 | 1425 |
| gtg gag acg tgt gag gag cgt ctc ctt gac ttg tag ccgccttctc<br>Val Glu Thr Cys Glu Glu Arg Leu Leu Asp Leu<br>               425              430 | 1471 |
| ctctgtccag gaggccggga tcaggctgtt gccatggaag ttcagggcca tagactgccc | 1531 |
| cacttaaact cttgtcagtc tgggctcagg gttcccagag ctcattcccc aggaatctct | 1591 |
| aagaccaggg ctggggcagt gtctgtcact ggcttgtttg ttccctacca atattctgtt | 1651 |
| gctgtttgaa gtagtgccag gtcccctgg aagatgccc ccaagacacc tgccccaagt | 1711 |
| gggtggatat ctgccttcct gctgcaagtg gaggcaggtc cagcagcccc tcttcagagc | 1771 |
| ccctgtaaat gctatcgcag cctgagtcct gccgccttcc agttccttgg tgtcccgtgc | 1831 |
| accccttctg tctgtcccct ttcatggctg tgcagccgtc ccgctggagt ggccatgtcc | 1891 |
| cttgtgcatt gagtgcatcc ccgctggtga ctaagctcgc agcaagcggc taccccccga | 1951 |
| tctgcaaaag ggcctctccc tttgtgttct atacattgtg aatcttcccg tctgaagaac | 2011 |
| gcccagcctg cccagacaaa gccccgcctt ccccaaagca gagggctgt ctgtgtctcc | 2071 |
| agaaagggga catcgggggg gagggggggct cagaaaggag aagggctgtg atctccggtc | 2131 |
| ccttcccccca tcatccttcc ttagactgat gctttgactg aatcatcact agctatggca | 2191 |
| ttaaaaggcc tctcttctca tctggtgcca aaggttccgt tgcagctttt tacaaccatc | 2251 |
| cggtgtggtt tggaggtttt gttttttttt tttcccaaca gaaagaaca gccattagaa | 2311 |
| gaaggctccc atttttctgat gttccgcccc actgtgaaga gtgtgctcgt tttaaattca | 2371 |
| tgttgattct tgtaagcact ggactgtctt catcaagtat ttccctacag aactcctcaa | 2431 |
| gaaaacagag atcatttggc tagagattgt ctgagtgact ccaagctact cactgtattg | 2491 |
| gacgggagta gtaatttatt ttaaagataa agtgactaag tggggaaatt tataaagcta | 2551 |

-continued

```
aatattatat atttattttt tcatacatgt ttgaagtgca aatctgtgga tattccattt    2611
gtaggaccaa gtcgacatgc ccatcctgac attgtatgct acgagaactc ttctgatgat    2671
ggaatttcga ttaaagtgca ctgaaagata aaaaaaaaaa aaaaaaaaaa aaaaaaaaaa    2731
aaaaaaaaaa aaaaa                                                    2746
```

<210> SEQ ID NO 2
<211> LENGTH: 431
<212> TYPE: PRT
<213> ORGANISM: Homo sapiens

<400> SEQUENCE: 2

```
Met Leu Ala Leu Leu Ala Ala Ser Val Ala Leu Ala Val Ala Ala Gly
1               5                   10                  15

Ala Gln Asp Ser Pro Ala Pro Gly Ser Arg Phe Val Cys Thr Ala Leu
            20                  25                  30

Pro Pro Glu Ala Val His Ala Gly Cys Pro Leu Pro Ala Met Pro Met
        35                  40                  45

Gln Gly Gly Ala Gln Ser Pro Glu Glu Leu Arg Ala Ala Val Leu
    50                  55                  60

Gln Leu Arg Glu Thr Val Val Gln Gln Lys Glu Thr Leu Gly Ala Gln
65                  70                  75                  80

Arg Glu Ala Ile Arg Glu Leu Thr Gly Lys Leu Ala Arg Cys Glu Gly
                85                  90                  95

Leu Ala Gly Gly Lys Ala Arg Gly Ala Gly Ala Thr Gly Lys Asp Thr
            100                 105                 110

Met Gly Asp Leu Pro Arg Asp Pro Gly His Val Val Glu Gln Leu Ser
        115                 120                 125

Arg Ser Leu Gln Thr Leu Lys Asp Arg Leu Glu Ser Leu Glu His Gln
    130                 135                 140

Leu Arg Ala Asn Val Ser Asn Ala Gly Leu Pro Gly Asp Phe Arg Glu
145                 150                 155                 160

Val Leu Gln Gln Arg Leu Gly Glu Leu Glu Arg Gln Leu Leu Arg Lys
                165                 170                 175

Val Ala Glu Leu Glu Asp Glu Lys Ser Leu Leu His Asn Glu Thr Ser
            180                 185                 190

Ala His Arg Gln Lys Thr Glu Ser Thr Leu Asn Ala Leu Leu Gln Arg
        195                 200                 205

Val Thr Glu Leu Glu Arg Gly Asn Ser Ala Phe Lys Ser Pro Asp Ala
    210                 215                 220

Phe Lys Val Ser Leu Pro Leu Arg Thr Asn Tyr Leu Tyr Gly Lys Ile
225                 230                 235                 240

Lys Lys Thr Leu Pro Glu Leu Tyr Ala Phe Thr Ile Cys Leu Trp Leu
                245                 250                 255

Arg Ser Ser Ala Ser Pro Gly Ile Gly Thr Pro Phe Ser Tyr Ala Val
            260                 265                 270

Pro Gly Gln Ala Asn Glu Ile Val Leu Ile Glu Trp Gly Asn Asn Pro
        275                 280                 285

Ile Glu Leu Leu Ile Asn Asp Lys Val Ala Gln Leu Pro Leu Phe Val
    290                 295                 300

Ser Asp Gly Lys Trp His His Ile Cys Val Thr Trp Thr Thr Arg Asp
305                 310                 315                 320

Gly Met Trp Glu Ala Phe Gln Asp Gly Glu Lys Leu Gly Thr Gly Glu
                325                 330                 335
```

-continued

```
Asn Leu Ala Pro Trp His Pro Ile Lys Pro Gly Gly Val Leu Ile Leu
            340                 345                 350

Gly Gln Glu Gln Asp Thr Val Gly Gly Arg Phe Asp Ala Thr Gln Ala
            355                 360                 365

Phe Val Gly Glu Leu Ser Gln Phe Asn Ile Trp Asp Arg Val Leu Arg
    370                 375                 380

Ala Gln Glu Ile Val Asn Ile Ala Asn Cys Ser Thr Asn Met Pro Gly
385                 390                 395                 400

Asn Ile Ile Pro Trp Val Asp Asn Asn Val Asp Val Phe Gly Gly Ala
                405                 410                 415

Ser Lys Trp Pro Val Glu Thr Cys Glu Arg Leu Leu Asp Leu
            420                 425                 430

<210> SEQ ID NO 3
<211> LENGTH: 2562
<212> TYPE: DNA
<213> ORGANISM: Rattus rattus
<220> FEATURE:
<221> NAME/KEY: CDS
<222> LOCATION: (128)..(1429)

<400> SEQUENCE: 3
tggtgctggc gtttccctgc ttgcacgcgg ttccctcgag cgccgctccg accgacgtag      60
ccggccgcga aggcgcccag acggcaagcc agcgacccat gctgaagtga gcgcccaggt    120 cagcgag atg ctg gcg ctg ctg acc gcc ggc gtg gcg ctc gcc gtg gcc     169
        Met Leu Ala Leu Leu Thr Ala Gly Val Ala Leu Ala Val Ala
          1               5                   10 gcg gga caa gcc cag gat aac ccg ata cct ggc agt cgc ttc gtg tgc     217
Ala Gly Gln Ala Gln Asp Asn Pro Ile Pro Gly Ser Arg Phe Val Cys
 15                  20                  25                  30 acc gcg ctg ccc ccc gaa gcg gcg cgc gcc ggc tgc ccg ctg ccc gcg     265
Thr Ala Leu Pro Pro Glu Ala Ala Arg Ala Gly Cys Pro Leu Pro Ala
                 35                  40                  45 atg ccc atg cag gga ggc gcg ctg agc cct gag gag gag ctg cga gcc     313
Met Pro Met Gln Gly Gly Ala Leu Ser Pro Glu Glu Glu Leu Arg Ala
             50                  55                  60 gct gtg ctg cac tgg cgc gag acc gtc gtg cag cag aag gag acg ctg     361
Ala Val Leu His Trp Arg Glu Thr Val Val Gln Gln Lys Glu Thr Leu
         65                  70                  75 ggc gct cag cga gaa gcc atc cga gaa ctc acc agc aag ctg gcc cgc     409
Gly Ala Gln Arg Glu Ala Ile Arg Glu Leu Thr Ser Lys Leu Ala Arg
     80                  85                  90 tgt gag gga cta gcc ggc ggt aag gcg cgc ggc acg ggg gcc acg ggc     457
Cys Glu Gly Leu Ala Gly Gly Lys Ala Arg Gly Thr Gly Ala Thr Gly
 95                 100                 105                 110 aag gac acc atg ggc gac ctg ccg cgg gac ccg ggc cac gtc gtg gag     505
Lys Asp Thr Met Gly Asp Leu Pro Arg Asp Pro Gly His Val Val Glu
                115                 120                 125 cag ctt agc cgc tcg ctg cag acc ctc aag gac cgc ttg gag agc ctc     553
Gln Leu Ser Arg Ser Leu Gln Thr Leu Lys Asp Arg Leu Glu Ser Leu
            130                 135                 140 gag ctc caa ctc cac acc aac gcg tct aat gcc ggg ctg ccg agc gac     601
Glu Leu Gln Leu His Thr Asn Ala Ser Asn Ala Gly Leu Pro Ser Asp
        145                 150                 155 ttc cga gag gtg ctc cag cgg agg ctg ggg gag ctg gag agg cag ttg     649
Phe Arg Glu Val Leu Gln Arg Arg Leu Gly Glu Leu Glu Arg Gln Leu
    160                 165                 170 cta cgc aag gtg gcc gag ctg gaa gac gag aag tcc ctg ctc cac aat     697
Leu Arg Lys Val Ala Glu Leu Glu Asp Glu Lys Ser Leu Leu His Asn
```

```
                        175                 180                 185                 190
gag acc tcg gct cac cgg cag aag aca gag aac aca ctg aat gca ctg      745
Glu Thr Ser Ala His Arg Gln Lys Thr Glu Asn Thr Leu Asn Ala Leu
                    195                 200                 205 ctg cag agg gtg act gag ctg gag aga ggc aac agt gca ttc aag tca      793
Leu Gln Arg Val Thr Glu Leu Glu Arg Gly Asn Ser Ala Phe Lys Ser
                210                 215                 220 cca gat gca ttc aaa gtg tcc ctc cct ctc cgt aca aac tac cta tac      841
Pro Asp Ala Phe Lys Val Ser Leu Pro Leu Arg Thr Asn Tyr Leu Tyr
            225                 230                 235 ggc aag atc aag aag acg ttg ccc gag ctg tat gcc ttc acc atc tgc      889
Gly Lys Ile Lys Lys Thr Leu Pro Glu Leu Tyr Ala Phe Thr Ile Cys
        240                 245                 250 ctg tgg ctg cgg tcc agc gcc tcg cca ggc atc ggc acg cca ttc tcc      937
Leu Trp Leu Arg Ser Ser Ala Ser Pro Gly Ile Gly Thr Pro Phe Ser
255                 260                 265                 270 tac gct gtg cct ggg caa gcc aat gag att gtg ctg ata gag tgg ggt      985
Tyr Ala Val Pro Gly Gln Ala Asn Glu Ile Val Leu Ile Glu Trp Gly
                275                 280                 285 aac aat ccc ata gag ctg ctt atc aac gac aag gtc gca cag ctg ccc     1033
Asn Asn Pro Ile Glu Leu Leu Ile Asn Asp Lys Val Ala Gln Leu Pro
            290                 295                 300 ctg ttt gtc agc gat ggc aag tgg cac cat atc tgc atc acc tgg acc     1081
Leu Phe Val Ser Asp Gly Lys Trp His His Ile Cys Ile Thr Trp Thr
        305                 310                 315 act cga gac ggc atg tgg gaa gca ttc cag gac ggg gag aag ctg ggc     1129
Thr Arg Asp Gly Met Trp Glu Ala Phe Gln Asp Gly Glu Lys Leu Gly
    320                 325                 330 acc ggg gag aac ctg gca ccc tgg cat ccc atc aag cca ggg ggt gtg     1177
Thr Gly Glu Asn Leu Ala Pro Trp His Pro Ile Lys Pro Gly Gly Val
335                 340                 345                 350 ctc atc ctg ggg cag gag cag gac act gtg gga ggc aga ttt gat gcc     1225
Leu Ile Leu Gly Gln Glu Gln Asp Thr Val Gly Gly Arg Phe Asp Ala
                355                 360                 365 aca cag gcc ttc gtt gga gag ctt agc cag ttc aac ata tgg gac cgt     1273
Thr Gln Ala Phe Val Gly Glu Leu Ser Gln Phe Asn Ile Trp Asp Arg
            370                 375                 380 gtc ctc cgg gca caa gag atc atc aac atc gcc aac tgc tcc acg aac     1321
Val Leu Arg Ala Gln Glu Ile Ile Asn Ile Ala Asn Cys Ser Thr Asn
        385                 390                 395 atg cct gga aac atc atc cca tgg gtg gac aac aat gtc gat gtg ttt     1369
Met Pro Gly Asn Ile Ile Pro Trp Val Asp Asn Asn Val Asp Val Phe
    400                 405                 410 gga ggg gct tcc aag tgg cct gtg gag acg tgc gaa gag cgt ctc ctg     1417
Gly Gly Ala Ser Lys Trp Pro Val Glu Thr Cys Glu Glu Arg Leu Leu
415                 420                 425                 430 gac ttg tag cta ccttctccct gtcccagagg ccaagagcgg gctgttctgg         1469
Asp Leu     Leu ggagttcaag gcatctattc ccgagttcaa ctaaaatctc tggcctgagt aggaaagaac   1529
cagagcccct aaggcaggct gtgtggcctc ctttgtctta ggctcctatg ttcttactgc   1589
tttgttcttt ggtgggaagt gaccgaagcc ctgggaagag tcctgagcca cttcctgctg   1649
gggtttctag taaagtctgt gagcctctcc accccctcctg taaatgctag tgcaacccag  1709
ccctgcctgt cattttggat ccttagtgtc tcgtgtgtgc ttcccgtctg tccccttttga  1769 tggctgtgtg gtcatcctac cggggtggcc tgggtccctt gtgtgtgtag cacatccctg   1829
cttttgactg aacacagtgc acagaagcta cccgcccctg aaacagggtc tctccctcag   1889
```

-continued

```
tgtcatgtgc actctggtct ctccctctga ggggactgca gctgctggag ggccacgtgc    1949
ccagacagtc cccagcatcc ccaaagcaga ccctccgcca tggagaaagt cccccacagc    2009
ttccccaccc tctgtccacc tctcagaccc cacgcttcta aggaccattg ctgggttggc    2069
tttcaaaagc tgctgctctc atctggtgcc aaaagttcat ttgcagcttc tacaccgttc    2129
tgtgtggttt ggggattgac tttattcccc cacaaaagag aacagccat tagaagccag     2189 cctcccctcc ttttgatgct cagcccactg tgaagagtga gcttgcttgt aagccacatt    2249
ggtttctgtg agcatctgac tctcccccgt ccagtatttt ccccggaact ggagattcga    2309
gtgccattcg gctgctacct gcttagtgac tccaggctgc atcatgtatc ataatttatt    2369
ttaaagacaa agtgattcag tggggaaatt tataaagcta taatattat atattttatt     2429 tttcatacat gtttaaagtg cggatccatg gatgttccat ttgtaggacc agcttgacgt    2489
gcccatcctg acattgtatg ccacaagagc tcttgtgatg atggaatttt gattaaagtg    2549
cactggaaga tga                                                        2562
```

<210> SEQ ID NO 4
<211> LENGTH: 432
<212> TYPE: PRT
<213> ORGANISM: Rattus rattus

<400> SEQUENCE: 4

```
Met Leu Ala Leu Leu Thr Ala Gly Val Ala Leu Ala Val Ala Ala Gly
1               5                   10                  15

Gln Ala Gln Asp Asn Pro Ile Pro Gly Ser Arg Phe Val Cys Thr Ala
            20                  25                  30

Leu Pro Pro Glu Ala Ala Arg Ala Gly Cys Pro Leu Pro Ala Met Pro
        35                  40                  45

Met Gln Gly Gly Ala Leu Ser Pro Glu Glu Leu Arg Ala Ala Val
    50                  55                  60

Leu His Trp Arg Glu Thr Val Val Gln Gln Lys Glu Thr Leu Gly Ala
65                  70                  75                  80

Gln Arg Glu Ala Ile Arg Glu Leu Thr Ser Lys Leu Ala Arg Cys Glu
                85                  90                  95

Gly Leu Ala Gly Gly Lys Ala Arg Gly Thr Gly Ala Thr Gly Lys Asp
            100                 105                 110

Thr Met Gly Asp Leu Pro Arg Asp Pro Gly His Val Val Glu Gln Leu
        115                 120                 125

Ser Arg Ser Leu Gln Thr Leu Lys Asp Arg Leu Glu Ser Leu Glu Leu
    130                 135                 140

Gln Leu His Thr Asn Ala Ser Asn Ala Gly Leu Pro Ser Asp Phe Arg
145                 150                 155                 160

Glu Val Leu Gln Arg Arg Leu Gly Glu Leu Glu Arg Gln Leu Leu Arg
                165                 170                 175

Lys Val Ala Glu Leu Glu Asp Glu Lys Ser Leu Leu His Asn Glu Thr
            180                 185                 190

Ser Ala His Arg Gln Lys Thr Glu Asn Thr Leu Asn Ala Leu Leu Gln
        195                 200                 205

Arg Val Thr Glu Leu Glu Arg Gly Asn Ser Ala Phe Lys Ser Pro Asp
    210                 215                 220

Ala Phe Lys Val Ser Leu Pro Leu Arg Thr Asn Tyr Leu Tyr Gly Lys
225                 230                 235                 240

Ile Lys Lys Thr Leu Pro Glu Leu Tyr Ala Phe Thr Ile Cys Leu Trp
                245                 250                 255
```

-continued

```
Leu Arg Ser Ser Ala Ser Pro Gly Ile Gly Thr Pro Phe Ser Tyr Ala
            260                 265                 270
Val Pro Gly Gln Ala Asn Glu Ile Val Leu Ile Glu Trp Gly Asn Asn
        275                 280                 285
Pro Ile Glu Leu Leu Ile Asn Asp Lys Val Ala Gln Leu Pro Leu Phe
    290                 295                 300
Val Ser Asp Gly Lys Trp His His Ile Cys Ile Thr Trp Thr Thr Arg
305                 310                 315                 320
Asp Gly Met Trp Glu Ala Phe Gln Asp Gly Glu Lys Leu Gly Thr Gly
                325                 330                 335
Glu Asn Leu Ala Pro Trp His Pro Ile Lys Pro Gly Gly Val Leu Ile
            340                 345                 350
Leu Gly Gln Glu Gln Asp Thr Val Gly Gly Arg Phe Asp Ala Thr Gln
        355                 360                 365
Ala Phe Val Gly Glu Leu Ser Gln Phe Asn Ile Trp Asp Arg Val Leu
    370                 375                 380
Arg Ala Gln Glu Ile Ile Asn Ile Ala Asn Cys Ser Thr Asn Met Pro
385                 390                 395                 400
Gly Asn Ile Ile Pro Trp Val Asp Asn Asn Val Asp Val Phe Gly Gly
                405                 410                 415
Ala Ser Lys Trp Pro Val Glu Thr Cys Glu Glu Arg Leu Leu Asp Leu
            420                 425                 430

<210> SEQ ID NO 5
<211> LENGTH: 1600
<212> TYPE: DNA
<213> ORGANISM: Mus musculus
<220> FEATURE:
<221> NAME/KEY: CDS
<222> LOCATION: (68)..(1357)

<400> SEQUENCE: 5
gccggccgcg aagcgcccag acggcaaacc agcgacccat gctgaagtga gcacacaggt        60 cagcgag atg ctg gcg ctg ctg acc gtc ggc gtg gcg ctc gcc gtg gcc       109
        Met Leu Ala Leu Leu Thr Val Gly Val Ala Leu Ala Val Ala
        1               5                   10 gcc gga cga gcc cag gac agc ccg ata cct ggc agc cgc ttc gtg tgc       157
Ala Gly Arg Ala Gln Asp Ser Pro Ile Pro Gly Ser Arg Phe Val Cys
15                  20                  25                  30 acc gcg ttg ccc ccc gaa gcg gcg cgc gcc ggt tgc ccg ctg ccc gcg       205
Thr Ala Leu Pro Pro Glu Ala Ala Arg Ala Gly Cys Pro Leu Pro Ala
                35                  40                  45 atg ccc atg cag gga ggc gct ctg agc ccc gag gag gag ctg cga gcc       253
Met Pro Met Gln Gly Gly Ala Leu Ser Pro Glu Glu Glu Leu Arg Ala
            50                  55                  60 gct gtg ctg cag ctg cgc gag acc gtc gtg cag cag aag gag acg ctg       301
Ala Val Leu Gln Leu Arg Glu Thr Val Val Gln Gln Lys Glu Thr Leu
        65                  70                  75 ggc gcc cag cga gaa gcc atc cga gag ctc acc ggc aag ctg gcc cgc       349
Gly Ala Gln Arg Glu Ala Ile Arg Glu Leu Thr Gly Lys Leu Ala Arg
    80                  85                  90 tgc gag ggg ctg gcg ggg ggc aag gcg cgc ggc aca ggc aag gac acc       397
Cys Glu Gly Leu Ala Gly Gly Lys Ala Arg Gly Thr Gly Lys Asp Thr
95                  100                 105                 110 atg ggc gac ctg ccg cgg gac ccg ggc cac gtc gtg gag cag ctt agc       445
Met Gly Asp Leu Pro Arg Asp Pro Gly His Val Val Glu Gln Leu Ser
                115                 120                 125
```

-continued

| | | |
|---|---|---|
| cgc tcc ttg caa acc ctc aag gac cgc ttg gag agc ctc gag ctc cag<br>Arg Ser Leu Gln Thr Leu Lys Asp Arg Leu Glu Ser Leu Glu Leu Gln<br>                130                135                140 | | 493 |
| ctc cgc aca aat gtg tct aac gct ggg ctg ccg agc gac ttc cga gag<br>Leu Arg Thr Asn Val Ser Asn Ala Gly Leu Pro Ser Asp Phe Arg Glu<br>                145                150                155 | | 541 |
| gtg ctc cag cgg agg ctc ggg gag ctg gag agg cag ttg cta cgc aag<br>Val Leu Gln Arg Arg Leu Gly Glu Leu Glu Arg Gln Leu Leu Arg Lys<br>    160                165                170 | | 589 |
| gtg gcg gag ctg gaa gat gag aag tcc ctg ctt cat aat gag acc tcg<br>Val Ala Glu Leu Glu Asp Glu Lys Ser Leu Leu His Asn Glu Thr Ser<br>175                180                185                190 | | 637 |
| gct cac cgg cag aag aca gag agc acg ctg aac gcc ctg ctg cag agg<br>Ala His Arg Gln Lys Thr Glu Ser Thr Leu Asn Ala Leu Leu Gln Arg<br>                195                200                205 | | 685 |
| gtg act gag ctg gag cga ggc aac agt gca ttc aag tca cca gat gca<br>Val Thr Glu Leu Glu Arg Gly Asn Ser Ala Phe Lys Ser Pro Asp Ala<br>    210                215                220 | | 733 |
| ttc aaa gtg tcc ctt cct ctc cgt aca aac tac ctg tat ggc aag atc<br>Phe Lys Val Ser Leu Pro Leu Arg Thr Asn Tyr Leu Tyr Gly Lys Ile<br>                225                230                235 | | 781 |
| aag aag aca ttg cct gag ctg tac gcc ttt acc atc tgc ctg tgg ctg<br>Lys Lys Thr Leu Pro Glu Leu Tyr Ala Phe Thr Ile Cys Leu Trp Leu<br>    240                245                250 | | 829 |
| cgg tcc agt gcc tcg cca ggc atc ggt acg cca ttc tcc tac gct gtg<br>Arg Ser Ser Ala Ser Pro Gly Ile Gly Thr Pro Phe Ser Tyr Ala Val<br>255                260                265                270 | | 877 |
| ccc ggg caa gcc aac gag att gtg ctg ata gag tgg ggc aat aac ccc<br>Pro Gly Gln Ala Asn Glu Ile Val Leu Ile Glu Trp Gly Asn Asn Pro<br>                275                280                285 | | 925 |
| att gag ctg ctc atc aac gac aag gtc gca cag ctg ccg ctg ttt gtc<br>Ile Glu Leu Leu Ile Asn Asp Lys Val Ala Gln Leu Pro Leu Phe Val<br>                290                295                300 | | 973 |
| agt gat ggc aag tgg cac cac atc tgc atc acc tgg acc act cga gac<br>Ser Asp Gly Lys Trp His His Ile Cys Ile Thr Trp Thr Thr Arg Asp<br>            305                310                315 | | 1021 |
| ggc atg tgg gaa gcg ttc cag gat ggg gag aag ctg ggc act ggg gaa<br>Gly Met Trp Glu Ala Phe Gln Asp Gly Glu Lys Leu Gly Thr Gly Glu<br>    320                325                330 | | 1069 |
| aac ctg gca ccc tgg cac ccc att aag cca ggg ggc gtg ctc atc ctg<br>Asn Leu Ala Pro Trp His Pro Ile Lys Pro Gly Gly Val Leu Ile Leu<br>335                340                345                350 | | 1117 |
| ggg cag gag cag gac acg gtg gga ggc aga ttt gat gcc acg cag gcc<br>Gly Gln Glu Gln Asp Thr Val Gly Gly Arg Phe Asp Ala Thr Gln Ala<br>                355                360                365 | | 1165 |
| ttt gtt gga gag ctc agc cag ttc aac ata tgg gac cgc gtc ctc cgg<br>Phe Val Gly Glu Leu Ser Gln Phe Asn Ile Trp Asp Arg Val Leu Arg<br>    370                375                380 | | 1213 |
| gcg cag gag atc atc aac atc gcc aac tgc tcc acg aac atg ccc ggc<br>Ala Gln Glu Ile Ile Asn Ile Ala Asn Cys Ser Thr Asn Met Pro Gly<br>385                390                395 | | 1261 |
| aac atc atc ccg tgg gtg gac aac aat gtc gat gtg ttc ggc ggg gct<br>Asn Ile Ile Pro Trp Val Asp Asn Asn Val Asp Val Phe Gly Gly Ala<br>    400                405                410 | | 1309 |
| tcc aag tgg cct gtg gag acc tgt gaa gag cgg ctc ctg gac ttg tag<br>Ser Lys Trp Pro Val Glu Thr Cys Glu Glu Arg Leu Leu Asp Leu<br>415                420                425 | | 1357 |
| ctgccctctc cgtcccagag gccacgatcc atcgggctgt tctgaggact tcaaggcatc | | 1417 |
| tcttccccat tcacctaaaa cctctggcct gaacagaaaa gagccggagc tctaatgcag | | 1477 |

-continued

```
gctgtgtggc cgcccttgtc ttaggctcat ttgttcctta ccattttgtc gaggtttttt    1537
ggggggtagt gacagaatcc ctggaagagt cttgagccac ttcctgctgg ggtttctgaa    1597
ttc                                                                  1600
```

<210> SEQ ID NO 6
<211> LENGTH: 429
<212> TYPE: PRT
<213> ORGANISM: Mus musculus

<400> SEQUENCE: 6

```
Met Leu Ala Leu Leu Thr Val Gly Val Ala Leu Ala Val Ala Ala Gly
  1               5                  10                  15

Arg Ala Gln Asp Ser Pro Ile Pro Gly Ser Arg Phe Val Cys Thr Ala
             20                  25                  30

Leu Pro Pro Glu Ala Ala Arg Ala Gly Cys Pro Leu Pro Ala Met Pro
         35                  40                  45

Met Gln Gly Gly Ala Leu Ser Pro Glu Glu Leu Arg Ala Ala Val
     50                  55                  60

Leu Gln Leu Arg Glu Thr Val Val Gln Gln Lys Glu Thr Leu Gly Ala
 65                  70                  75                  80

Gln Arg Glu Ala Ile Arg Glu Leu Thr Gly Lys Leu Ala Arg Cys Glu
                 85                  90                  95

Gly Leu Ala Gly Gly Lys Ala Arg Gly Thr Gly Lys Asp Thr Met Gly
            100                 105                 110

Asp Leu Pro Arg Asp Pro Gly His Val Val Glu Gln Leu Ser Arg Ser
        115                 120                 125

Leu Gln Thr Leu Lys Asp Arg Leu Glu Ser Leu Glu Leu Gln Leu Arg
    130                 135                 140

Thr Asn Val Ser Asn Ala Gly Leu Pro Ser Asp Phe Arg Glu Val Leu
145                 150                 155                 160

Gln Arg Arg Leu Gly Glu Leu Glu Arg Gln Leu Leu Arg Lys Val Ala
                165                 170                 175

Glu Leu Glu Asp Glu Lys Ser Leu Leu His Asn Glu Thr Ser Ala His
            180                 185                 190

Arg Gln Lys Thr Glu Ser Thr Leu Asn Ala Leu Leu Gln Arg Val Thr
        195                 200                 205

Glu Leu Glu Arg Gly Asn Ser Ala Phe Lys Ser Pro Asp Ala Phe Lys
    210                 215                 220

Val Ser Leu Pro Leu Arg Thr Asn Tyr Leu Tyr Gly Lys Ile Lys Lys
225                 230                 235                 240

Thr Leu Pro Glu Leu Tyr Ala Phe Thr Ile Cys Leu Trp Leu Arg Ser
                245                 250                 255

Ser Ala Ser Pro Gly Ile Gly Thr Pro Phe Ser Tyr Ala Val Pro Gly
            260                 265                 270

Gln Ala Asn Glu Ile Val Leu Ile Glu Trp Gly Asn Asn Pro Ile Glu
        275                 280                 285

Leu Leu Ile Asn Asp Lys Val Ala Gln Leu Pro Leu Phe Val Ser Asp
    290                 295                 300

Gly Lys Trp His His Ile Cys Ile Thr Trp Thr Thr Arg Asp Gly Met
305                 310                 315                 320

Trp Glu Ala Phe Gln Asp Gly Glu Lys Leu Gly Thr Gly Glu Asn Leu
                325                 330                 335

Ala Pro Trp His Pro Ile Lys Pro Gly Gly Val Leu Ile Leu Gly Gln
```

-continued

```
            340                 345                 350

Glu Gln Asp Thr Val Gly Gly Arg Phe Asp Ala Thr Gln Ala Phe Val
        355                 360                 365

Gly Glu Leu Ser Gln Phe Asn Ile Trp Asp Arg Val Leu Arg Ala Gln
    370                 375                 380

Glu Ile Ile Asn Ile Ala Asn Cys Ser Thr Asn Met Pro Gly Asn Ile
385                 390                 395                 400

Ile Pro Trp Val Asp Asn Asn Val Asp Val Phe Gly Gly Ala Ser Lys
                405                 410                 415

Trp Pro Val Glu Thr Cys Glu Glu Arg Leu Leu Asp Leu
            420                 425

<210> SEQ ID NO 7
<211> LENGTH: 133
<212> TYPE: PRT
<213> ORGANISM: Oxyuranus scutellatus

<400> SEQUENCE: 7

Ser Glu Leu Pro Gln Pro Ser Ile Asp Phe Glu Gln Phe Ser Asn Met
1               5                   10                  15

Ile Gln Cys Thr Ile Pro Cys Gly Ser Glu Cys Leu Ala Tyr Met Asp
            20                  25                  30

Tyr Gly Cys Tyr Cys Gly Pro Gly Gly Ser Gly Thr Pro Ile Asp Asp
        35                  40                  45

Leu Asp Arg Cys Cys Lys Thr His Asp Glu Cys Tyr Ala Glu Ala Gly
    50                  55                  60

Lys Leu Ser Ala Cys Lys Ser Val Leu Ser Glu Pro Asn Asn Asp Thr
65                  70                  75                  80

Tyr Ser Tyr Glu Cys Asn Glu Gly Gln Leu Thr Cys Asn Asp Asp Asn
                85                  90                  95

Asp Glu Cys Lys Ala Phe Ile Cys Asn Cys Asp Arg Thr Ala Val Thr
            100                 105                 110

Cys Phe Ala Gly Ala Pro Tyr Asn Asp Asp Leu Tyr Asn Ile Gly Met
        115                 120                 125

Ile Glu Cys His Lys
    130
```